United States Patent
Liu et al.

(10) Patent No.: US 11,129,909 B2
(45) Date of Patent: Sep. 28, 2021

(54) CONJUGATE AND BLOCK COPOLYMER CONTAINING FLUORESCENT CHROMOPHORE AND PREPARATION METHOD THEREFOR AND USE THEREOF

(71) Applicant: University of Science and Technology of China, Hefei (CN)

(72) Inventors: Shiyong Liu, Hefei (CN); Guhuan Liu, Hefei (CN); Yanyan Jiang, Hefei (CN)

(73) Assignee: University of Science and Technology of China, Anhui (CN)

( * ) Notice: Subject to any disclaimer, the term of this patent is extended or adjusted under 35 U.S.C. 154(b) by 62 days.

(21) Appl. No.: 16/611,191

(22) PCT Filed: May 16, 2017

(86) PCT No.: PCT/CN2017/084503
§ 371 (c)(1),
(2) Date: Nov. 5, 2019

(87) PCT Pub. No.: WO2018/205286
PCT Pub. Date: Nov. 15, 2018

(65) Prior Publication Data
US 2020/0155707 A1 May 21, 2020

(30) Foreign Application Priority Data

May 8, 2017 (CN) .......................... 201710316952.8
May 8, 2017 (CN) .......................... 201710317186.7
May 8, 2017 (CN) .......................... 201710317704.5

(51) Int. Cl.
| | | |
|---|---|---|
| A61B 5/00 | (2006.01) | |
| A61B 8/00 | (2006.01) | |
| A61B 10/00 | (2006.01) | |
| A61K 49/00 | (2006.01) | |
| C07K 14/585 | (2006.01) | |
| C07K 14/765 | (2006.01) | |

(52) U.S. Cl.
CPC ...... *A61K 49/0019* (2013.01); *A61K 49/0056* (2013.01); *A61K 49/0058* (2013.01); *C07K 14/585* (2013.01); *C07K 14/765* (2013.01)

(58) Field of Classification Search
None
See application file for complete search history.

(56) References Cited

U.S. PATENT DOCUMENTS

| 4,585,862 A | 4/1986 | Wang et al. |
| 2014/0328764 A1 | 11/2014 | Tang et al. |
| 2016/0356723 A1 | 12/2016 | Liu et al. |

FOREIGN PATENT DOCUMENTS

| CN | 101792516 A | 8/2010 |
| CN | 102153541 A | 8/2011 |
| CN | 102657873 A | 9/2012 |
| CN | 103842472 A | 6/2014 |
| CN | 104004149 A | 8/2014 |
| | (Continued) | |

OTHER PUBLICATIONS

International Search Report and Written Opinion for International Application No. PCT/CN2017/084503, dated Feb. 13, 2018.
(Continued)

*Primary Examiner* — Michael G. Hartley
*Assistant Examiner* — Melissa J Perreira
(74) *Attorney, Agent, or Firm* — Wolf, Greenfield & Sacks, P.C.

(57) ABSTRACT

A conjugate containing a fluorescent chromophore, which has any structure selected from C1 to C3. The conjugate containing the fluorescent chromophore provided by the described embodiments includes one fluorescent chromophore and two highly reactive groups R1 and R2 linked to the fluorescent chromophore by a covalent bond. The fluorescent chromophore in the conjugate initially has no or only weak fluorescence emission capability, and only after the two highly reactive groups react together with the corresponding molecule, the fluorescent chromophore has strong fluorescence emission. Therefore, the efficiency of conjugation of drug molecules to targeting molecules can be monitored in situ by the infrared fluorescence emission intensity and applied to the target-mediated drug delivery.

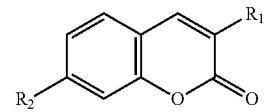

C1

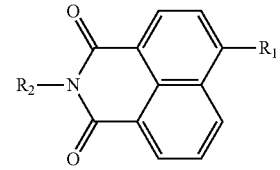

C2

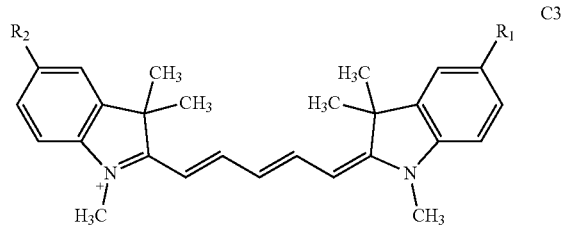

C3

17 Claims, 13 Drawing Sheets

(56) References Cited

FOREIGN PATENT DOCUMENTS

| CN | 105669657 A | 6/2016 |
|----|-------------|--------|
| CN | 105732681 A | 7/2016 |
| CN | 106461641 A | 2/2017 |

OTHER PUBLICATIONS

Wang et al., Aminonaphthalimide-based Imidazolium Podands for Turn-On Fluorescence Sensing of Nucleoside Polyphosphates. Organic & Biomolecular Chiemisty. 2010;8:2923.

Sato et al., Synthesis and spectral properties of polymethine-cyanine dye—nitroxide radical hybrid compounds for use as fluorescence probes to monitor reducing species and radicals. Spectrochimica Acta Part A: Molecular and Biomolecular Spectroscopy. Jan. 1, 2009;71(5):2030-9.

blue channel:coumarin / green channel:naphthalimide

CONJUGATE AND BLOCK COPOLYMER CONTAINING FLUORESCENT CHROMOPHORE AND PREPARATION METHOD THEREFOR AND USE THEREOF

This application is a national stage filing under 35 U.S.C. 371 of International Patent Application Serial No. PCT/CN2017/084503, filed May 16, 2017, which claims priority to Chinese Patent Application No. 201710317704.5, filed on May 8, 2017, titled "FLUOROPHORE-CONTAINING CONJUGATE, SEGMENTED COPOLYMER, TARGETED DRUG AND PREPARATION METHOD AND APPLICATION THEREOF"; priority to Chinese Patent Application No. 201710316952.8, filed on May 8, 2017, titled "ANTIBODY-DRUG/PROBE CONJUGATE WITH FLUORESCENCE EMISSION PROPERTY AND PREPARATION METHOD AND APPLICATION THEREOF"; and priority to Chinese Patent Application No. 201710317186.7, filed on May 8, 2017, titled "PROTEIN/POLYPEPTIDE-POLYMER CONJUGATE WITH FLUORESCENCE EMISSION PROPERTY AS WELL AS PREPARATION METHOD AND APPLICATION THEREOF", the contents of these applications are incorporated herein by reference in their entirety.

FIELD

The present disclosure relates to the technical field of organic bridging molecule, specifically to a conjugate and a block copolymer containing fluorescent chromophore, and preparation method therefor and use thereof.

BACKGROUND

Covalent functionalization of polypeptides, proteins and antibodies with synthetic polymers, drugs and imaging probes has formed important bioconjugates for clinical use. Protein-polymer conjugates, together with antibody-drug conjugates, become typical examples. Protein-polymer conjugates can date back to 1970. Davis, Abuchowski and co-workers reported the coupling of polyethylene glycol (PEG) with bovine serum albumin. This technology is now known as PEGylation, and extends to many polymer types, such as responsive polymers and zwitterionic polymers. Bonding the synthesized polymers to proteins, such as PEGylation, can bring many advantages, including enhanced protein solubility and stability, reduced immunogenicity, and increased blood circulation half-life. Currently at least PEGylated protein has been approved by the US Food and Drug Administration (FDA). On the other hand, binding of antibody drug conjugates (ADCs) to monoclonal antibodies that specifically target the lesion may kill cancer cells. Two FDA-approved ADCs, brentuximabvedotin (trade name, Adcetris) and trastuzumab (trade name, Kadcyla), are currently commercially available, and about 40 ADCs are clinically used currently.

Protein-polymer conjugates are prepared by methods of grafting from, grafting to and grafting through. The preparation of antibody-drug conjugates and protein-polymers relies on the selection of suitable highly efficient coupling reactions and linking groups. For protein/antibody conjugates, a selection which does not affect the protein/drug activity and the antibody function is the best. Typically, this can be achieved by modification of the natural protein specific site of protein/antibody tissue engineering (for example, reduction of disulfide bonds, modification of carbon ends, or oxidation of polysaccharides), and directly by specific reactions of specific amino acid. Covalently bonding of the synthesized functional polymer/drug to the protein/antibody mainly uses an orthogonal click reaction, such as Staudinger reaction, copper-catalyzed azide-alkyne cycloaddition (CuAAC), tension-promoted azide-cycloalkyne cycloaddition (SPAAC), D-A reaction, Michael reaction, and formation of oximes/hydrazone from aldehydes and ketones. The introduction of new design principles, such as modular design, gentle synthesis, optical tracing and multi-functional integration capacity, further contributes to the development of the field.

It is worth noting that even for optimally designed protein-polymer conjugates, a significant reduction in protein function and activity is unavoidable. One solution is to prepare a cleavable bioconjugate that releases the natural protein in-vivo over time. During cell internalization, ADCs should be able to effectively release their active drug load to exhibit cytotoxicity. However, monitoring shows that the degree of coupling of protein-polymer conjugates and antibody-drug conjugates and the subsequent release of proteins/drugs largely depends on traditional ex situ techniques. For example, sodium dodecyl sulfate-polyacrylamide gel electrophoresis (SDS-PAGE), mass spectrometry (MS), high performance liquid chromatography (HPLC), and size exclusion chromatography (SEC). This prevents real-time monitoring of the release process of the polymer/drug conjugate at in-vitro and in cellular levels.

In addition, imaging of antibody-directed optical molecules exhibits great potential in medical diagnostic and therapeutic response evaluation; and it can also be directly combined with surgical or endoscopic procedures. Targeted antibodies labeled with fluorescent probes can be imaged in real time with high resolution in vivo, and can be used for initial detection and monitoring of residual cancer tissue during surgery. However, probes with continuous fluorescence have inherent defects such as background interference and low signal-to-noise ratio.

Antibody-drug conjugates are capable of reducing systemic toxicity and enhancing the therapeutic efficiency of the conjugate drug. Design of the connecting bond in an antibody-drug conjugate is critical because it not only requires providing sufficient stability for systemic circulation of the masking drug, but also rapidly and efficiently releasing drug within the tumor cell. Triggerable cleavable linkages are often used to link drugs and antibodies. However, currently, the quantification of coupling efficiency and post-trigger release degree largely depends on ex-situ techniques such as high performance liquid chromatography, gel electrophoresis, size exclusion chromatography, and mass spectrometry. Currently, real-time monitoring of the release process of antibody-drug conjugates at in vitro and in cellular levels has not yet been achieved.

SUMMARY

In view of this, the technique problem to be solved by the present disclosure is to provide a conjugate and a block copolymer containing fluorescent chromophore, and preparation method therefor and use thereof, which can in-situ monitor conjugate efficiency of the conjugate by an infrared fluorescence emission intensity, and be used in the delivery of targeted mediated drug, or the delivery of polypeptide and anti-cancer drugs.

The present disclosure provides a conjugate containing a fluorescent chromophore, which has any of the following structures:

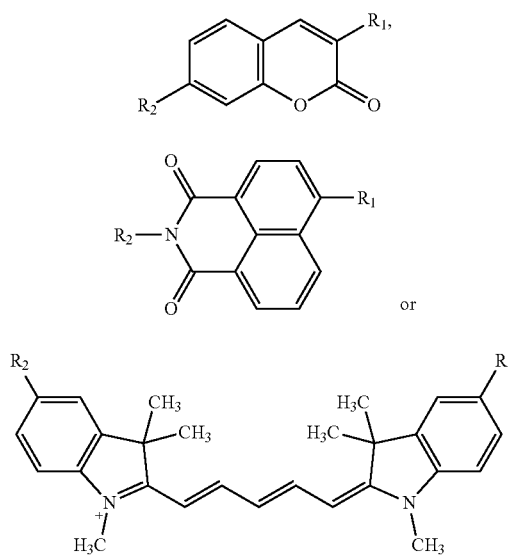

wherein R₁ and R₂ are groups that are able to quench fluorescence of fluorescent chromophore and are able to carry out a "click" reaction.

Preferably,

R₁ is

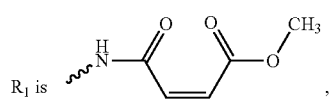
R1-1

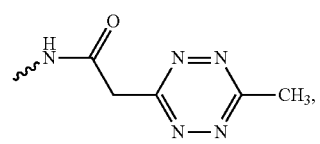
R1-2

$\sim\!\!\sim\!\!\sim N_3$ or
R1-3

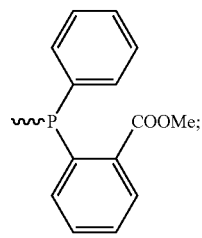
R1-4 and

R₂ is

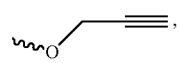
R2-1

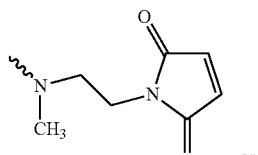
R2-2

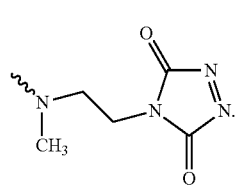
R2-3 or

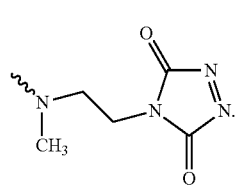
R2-4

The present disclosure provides a block copolymer having fluorescence emission properties, which has a structure as shown in Formula I-1:

Formula I-1

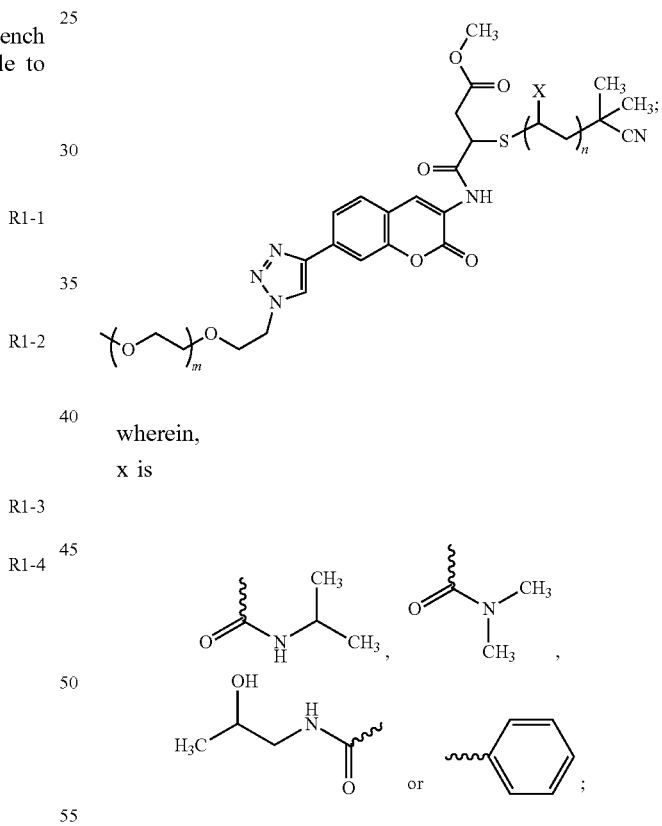

wherein, x is

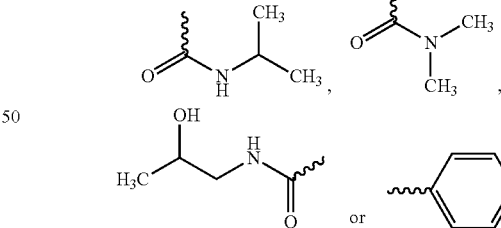

and m is 23-445, and n is 10-150.

The present disclosure provides a method for preparing the block copolymer having fluorescence emission properties, comprising steps of:

performing a Michael reaction and a click reaction on a polymer B containing a sulfhydryl end group and a polymer C containing an azide group and a chemical conjugated molecule D, to obtain the block copolymer as shown in the Formula I-1;

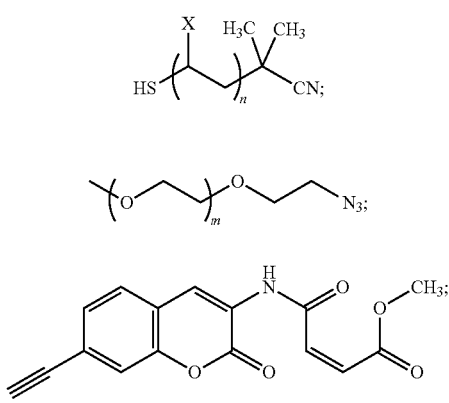

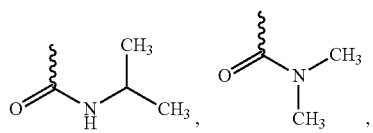

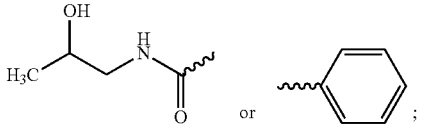

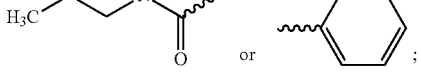

wherein,
x is and
m is 23-445, and n is 10-150.

Preferably, a conjugation efficiency of the block copolymer is in-situ monitored by fluorescence emission intensity.

The present disclosure provides a targeted drug having fluorescence emission properties, which has a structure as shown in Formula II-1:

Formula II-1

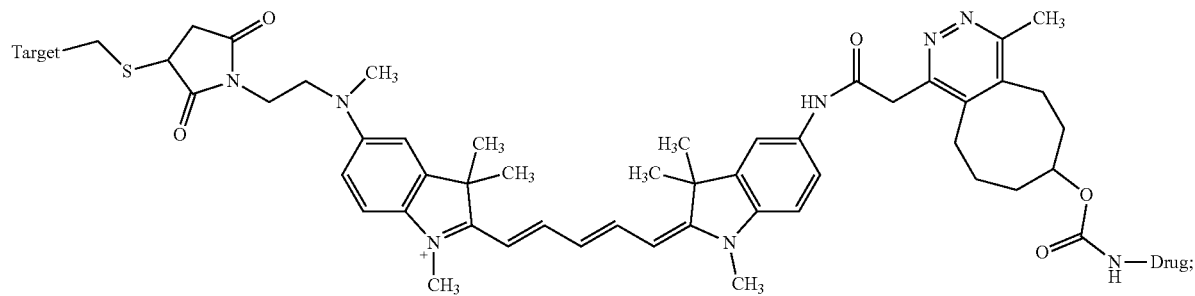

wherein,
Target is a cyclic RGD polypeptide, folic acid or sulfamide; and
Drug is doxorubicin, camptothecin or paclitaxel.

The present disclosure provides a method for preparing the targeted drug having fluorescence emission properties, comprising steps of:

performing a Michael reaction and a retro-D-A reaction on a targeted molecule F, a drug molecule G and a chemical conjugated molecule H, to obtain the targeted drug as shown in the Formula II-1;

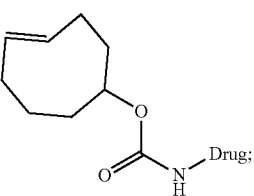

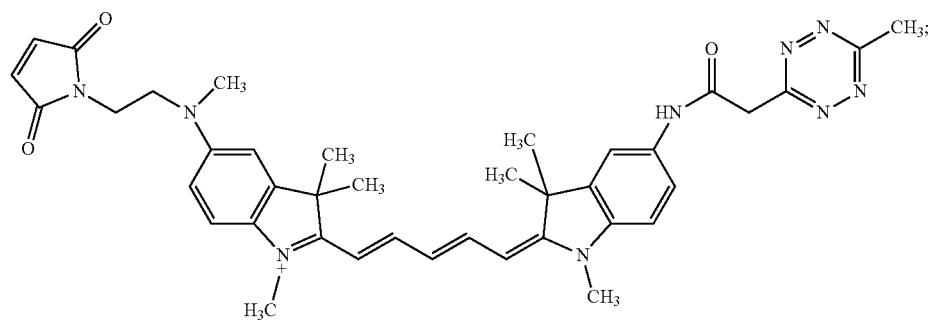

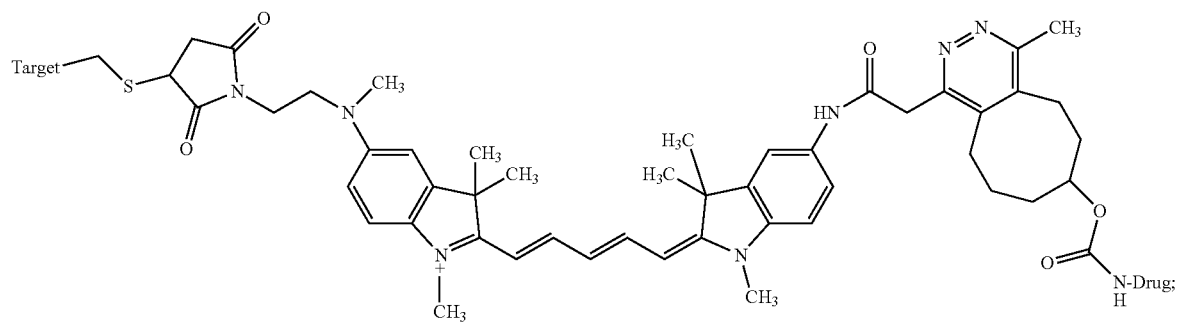

Formula II-1 wherein,

Target is a cyclic RGD polypeptide, folic acid or sulfamide; and

Drug is doxorubicin, camptothecin or paclitaxel.

Preferably, a conjugation efficiency of the drug molecule and the targeted molecule is in-situ monitored by infrared fluorescence emission intensity.

The present disclosure provides use of the targeted drug in delivery of a targeted mediated drug.

The conjugate containing fluorescent chromophore provided by the present disclosure comprises a fluorescent chromophore and two highly reactive groups $R_1$ and $R_2$ connected to the fluorescent chromophore by a covalent bond. The fluorescent chromophore in the conjugate initially has no or only weak fluorescence emission capability, and only after the two highly reactive groups react together with the corresponding molecule, the fluorescent chromophore has strong fluorescence emission. Therefore, the conjugation efficiency of the drug molecules and the targeting molecules can be in-situ monitored by infrared fluorescence emission intensity, which can be applied to the target-mediated drug delivery, and used in real-time monitoring of the release of polymer/drug conjugate in-vitro or in cell levels.

The present disclosure provides an antibody-drug/probe conjugate having fluorescence emission properties, which comprises a structure as shown in Formula I-2:

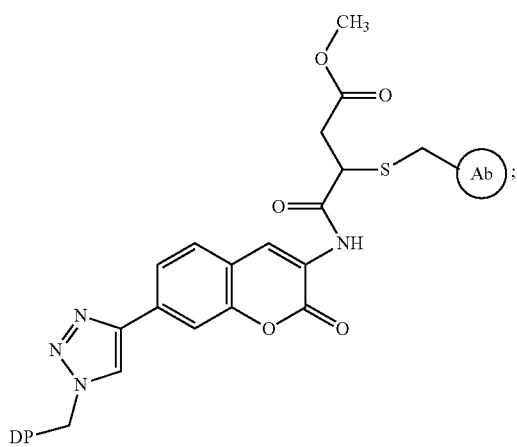

Formula I-2 wherein,

Ab is an antibody, and DP is a fluorescence probe or a drug molecule.

The present disclosure provides an antibody-probe conjugate having fluorescence emission properties, which has a structure as shown in Formula II-2:

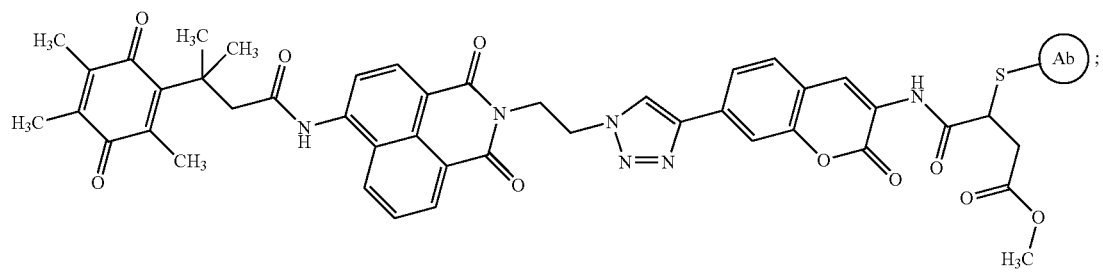

Formula II-2 wherein Ab is a carcinoembryonic antigen monoclonal antibody or Herceptin.

The present disclosure provides a method for preparing the above antibody-probe conjugate, comprising steps of:

performing a Michael reaction and a click reaction on a monoclonal antibody, a fluorescence probe A containing an azide group and a bifunctional fluorescent molecule D, to obtain the antibody-probe conjugate as shown in Formula II-2;

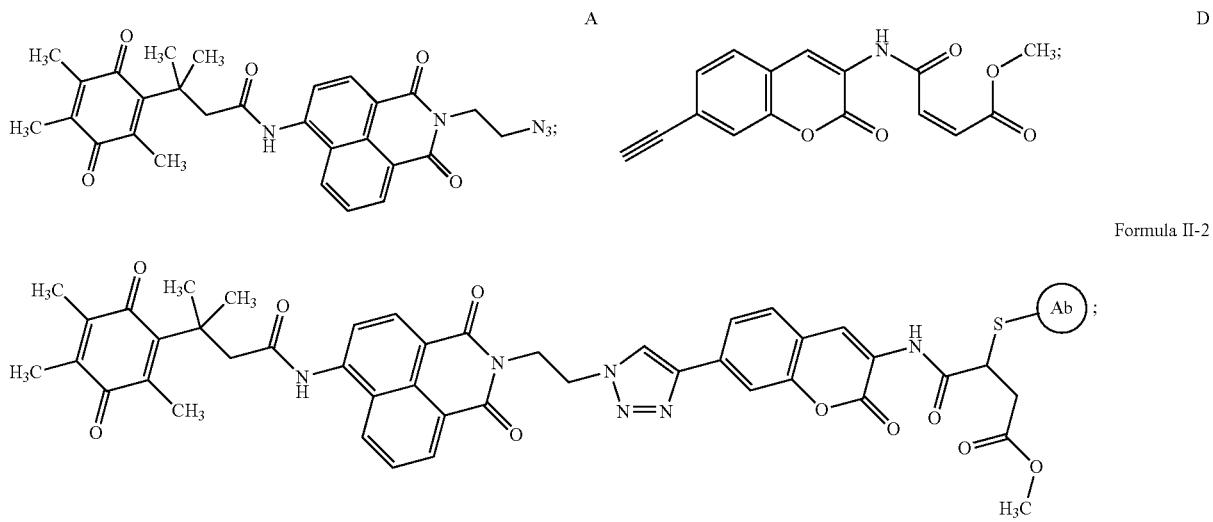

Formula II-2 wherein, the monoclonal antibody is a carcinoembryonic antigen monoclonal antibody or Herceptin containing a sulfhydryl group Preferably, a conjugation efficiency of the antibody-probe conjugate is in-situ monitored by fluorescence emission intensity.

The present disclosure provides use of the above antibody-probe conjugate or the antibody-probe conjugate prepared by the above method as a reaction indicator of an antigen and a quinone oxidoreductase.

The present disclosure provides an antibody-drug conjugate having fluorescence emission properties, which has a structure as shown in Formula III:

Formula III wherein, DOX is doxorubicin, and Ab is a carcinoembryonic antigen monoclonal antibody or Herceptin.

The present disclosure provides a method for preparing the above antibody-drug conjugate, comprising steps of:

performing a Michael reaction and a click reaction on a monoclonal antibody, a prodrug molecule E containing an azide group and a bifunctional fluorescent molecule D, to obtain the antibody-drug conjugate as shown in Formula III;

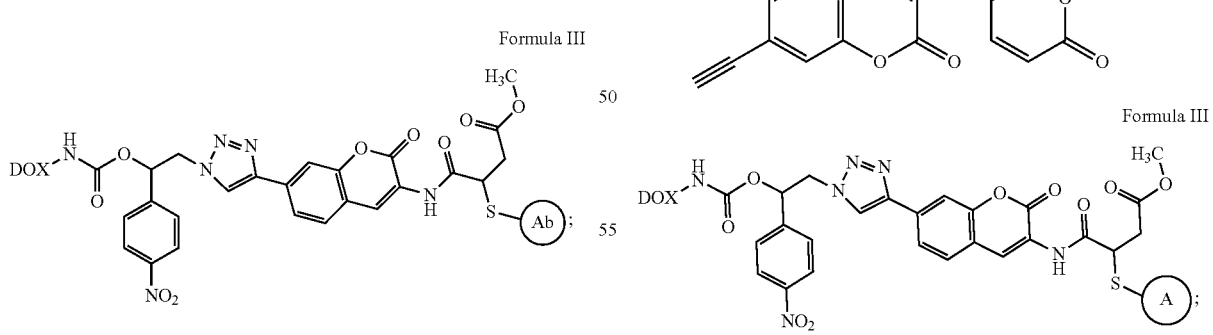

Formula III wherein DOX is doxorubicin, and the monoclonal antibody is a carcinoembryonic antigen monoclonal antibody or Herceptin containing a sulfhydryl group.

Preferably, a conjugation efficiency of the antibody-drug conjugate is in-situ monitored by fluorescence emission intensity.

The present disclosure provides use of the above antibody-drug conjugate or the antibody-drug conjugate prepared by the above method as a fluorescent indicator in real-time monitoring drug release.

The present disclosure provides use of the above antibody-drug conjugate or the antibody-drug conjugate prepared by the above method as a targeted drug release carrier.

The antibody-drug/probe conjugate provided in the present disclosure has a feature of self-reported conjugation efficiency, which bridges an antibody and a probe/drug molecule by a bifunctional fluorescent molecule. The bifunctional fluorescent molecule itself has no or only weak fluorescence emission capability, and only after the antibody-probe/drug is conjugated, the florescent molecule has strong fluorescence emission. Therefore, the conjugation process can be in-situ monitored by fluorescence monitoring, and the antibody-drug/probe conjugate can be applied to the delivery of therapeutic polypeptide and anti-cancer drugs.

The present disclosure provides a protein/polypeptide-polymer conjugate having fluorescence emission properties, which has a structure as shown in Formula I-3:

Formula I-3

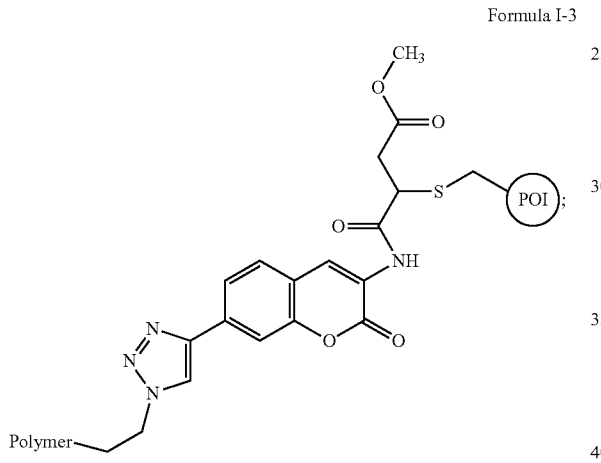

wherein, POI is a protein or a polypeptide; and Polymer is a polymer.

The present disclosure provides a protein-polymer conjugate having fluorescence emission properties, which has a structure as shown in Formula I-a:

Formula I-a

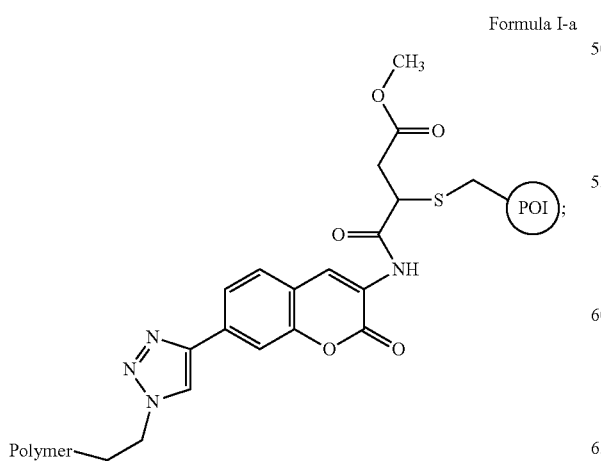

wherein, POI is a bovine serum albumin or a salcatonin, and Polymer is a polyethylene glycol.

The present disclosure provides a method for preparing the protein-polymer conjugate, comprising steps of:

performing a Michael reaction and a click reaction on a bovine serum albumin containing a sulfhydryl group, a polyethylene glycol containing an azide end group and compound D, to obtain a protein-polymer conjugate as shown in Formula I-a;

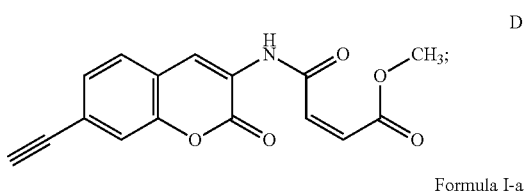

Formula I-a

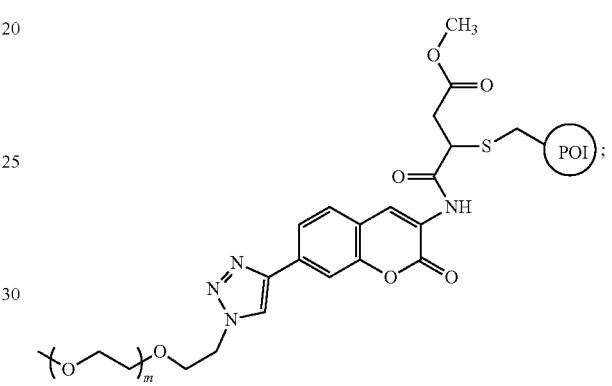

wherein POI is a bovine serum albumin, m is 23-445;

or comprising steps of:

performing a Michael reaction and a click reaction on a salcatonin containing a sulfhydryl group, a polyethylene glycol containing an azide end group and compound D, to obtain a protein-polymer conjugate as shown in Formula I-a; wherein POI is a salcatonin; and m is 23-445.

The present disclosure provides a polypeptide-polymer conjugate having fluorescence emission properties, which has a structure as shown in Formula I-b:

Formula I-b

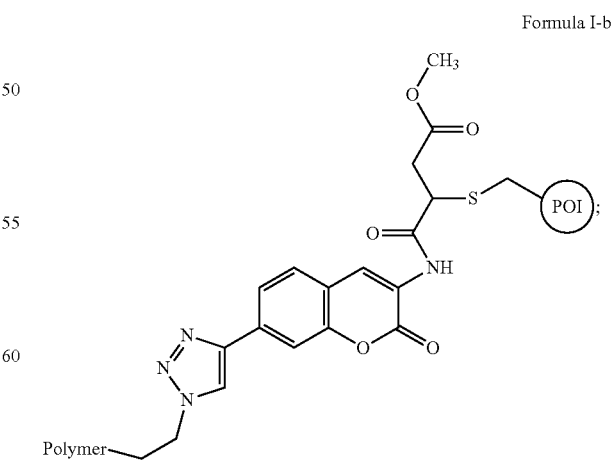

wherein, POI is a matrix metalloproteinase cleavable polypeptide, and Polymer is a polytrimethylene carbonate.

The present disclosure provides a method for preparing the above polypeptide-polymer conjugate, comprising steps of:

performing a Michael reaction and a click reaction on a matrix metalloproteinase cleavable polypeptide as shown in Formula J, a polytrimethylene carbonate containing an azide end group as shown in Formula K and compound D, to obtain the polypeptide-polymer conjugate as shown in Formula I-b;

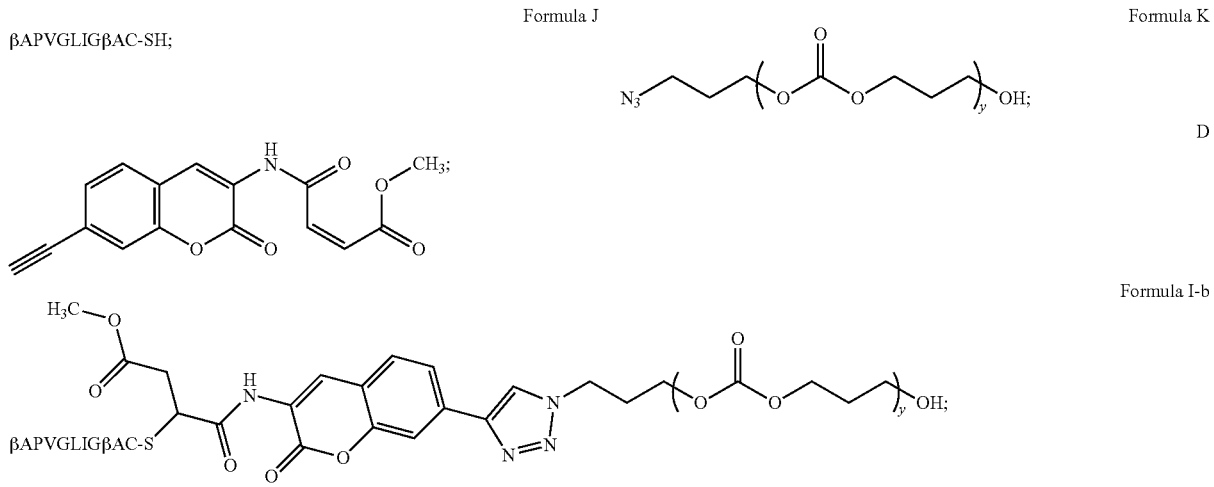

wherein y is 10-55.

Preferably, in the above method, a conjugation efficiency of the conjugate is in-situ monitored by fluorescence emission intensity.

The present disclosure provides a polymer vesicle consisting of the above polypeptide-polymer conjugate or the polypeptide-polymer conjugate prepared by the above method.

Preferably, the polymer vesicle has a particle diameter of 60-150 nm.

The polymer vesicle has a property of matrix metalloproteinase response.

The present disclosure provides use of the above polymer vesicle as a drug carrier, or as a fluorescent indicator in real-time monitoring drug release.

The protein/polypeptide-polymer conjugate provided by the present disclosure bridges the protein/polypeptide and the polymer by a bifunctional fluorescent molecule. The bifunctional fluorescent molecule itself has no or only weak fluorescence emission capability, and only after the protein/polypeptide-polymer is conjugated, the florescent molecule has strong fluorescence emission. Therefore, the conjugation process of the protein/polypeptide-polymer conjugate can be in-situ monitored by fluorescence changes, and the protein/polypeptide-polymer conjugate can be applied to the delivery of therapeutic polypeptide and anti-cancer drugs.

DETAILED DESCRIPTION

Figure 1:
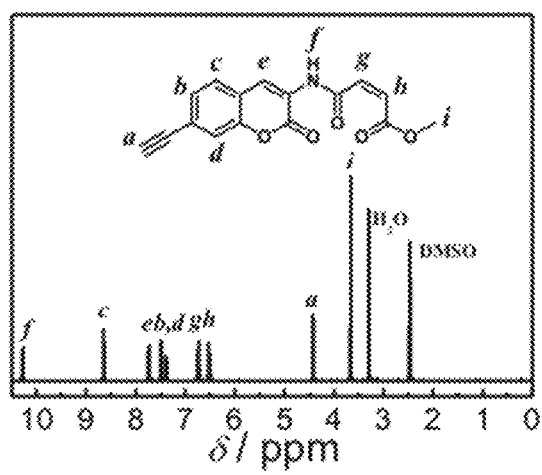
FIG. 1 shows the hydrogen nuclear magnetic resonance spectroscopy of C1 prepared in the present disclosure.

The present disclosure provides a conjugate containing fluorescent chromophore, which has any of the following structures:

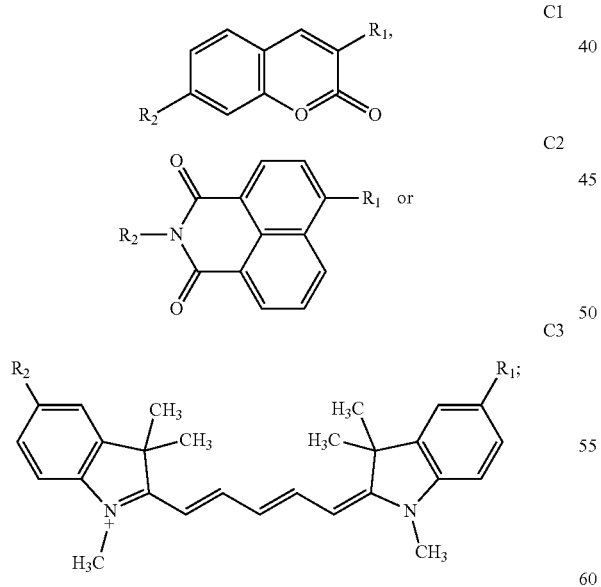

wherein $R_1$ and $R_2$ are groups that are able to quench fluorescence of the fluorescent chromophore and are able to carry out a "click" reaction.

The conjugate containing fluorescent chromophore provided by the present disclosure comprises a fluorescent chromophore and two highly reactive groups $R_1$ and $R_2$ connected to the fluorescent chromophore by a covalent bond. The fluorescent chromophore in the conjugate initially has no or only weak fluorescence emission capability, and only after the two highly reactive groups react together with the corresponding molecule, the fluorescent chromophore has strong fluorescence emission. The conjugates are as shown in formulas C1-C3, wherein the fluorescent chromophore in C1 is a coumarin group, the fluorescent chromophore in C2 is a naphthalimide group, and the fluorescent chromophore in C3 is a pentamethine group.

Preferably,
$R_1$ is

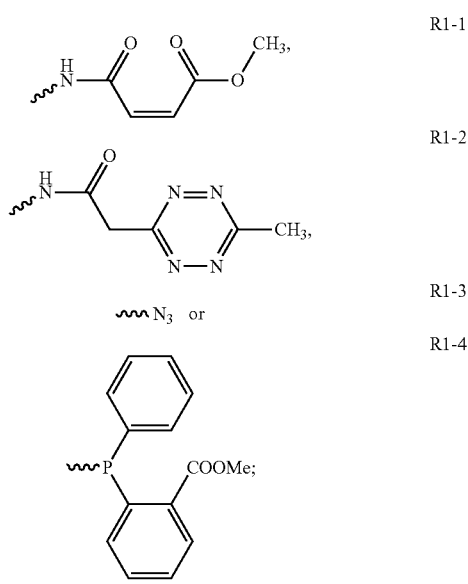

and
$R_2$ is

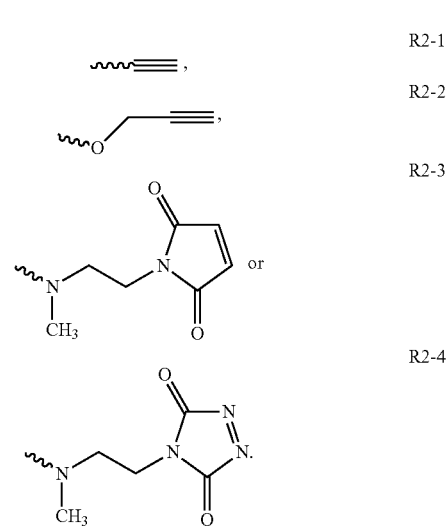

In the present disclosure, the curve represents for the connecting bond.

In the present disclosure, the species of the molecule reacting with the above conjugate depend on $R_1$ and $R_2$. R1-1 and R2-3 correspond to molecules containing a sulfhydryl group, R1-2 corresponds to molecules containing a trans-cyclooctenyl group, R1-3 corresponds to molecules containing a alkynyl group, R1-4 and R2-1, R2-2 correspond to molecules containing an azide group, and R2-4 corresponds to molecules containing a butadienyl group.

In the present disclosure, a polymer containing the above specific reactive group, a targeted molecule or a drug molecule reacts with the above conjugate to obtain the block polymer or targeted drug having fluorescence emission properties.

Specifically, the present disclosure provides a block copolymer having fluorescence emission properties, which is prepared by using the above conjugate as a bridging molecule, and has a structure as shown in Formula I-1:

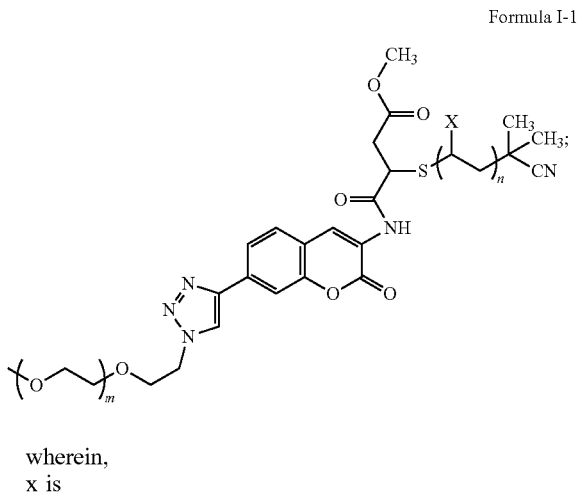

Formula I-1 wherein,
x is and
m is 23-445, and n is 10-150.

The present disclosure provides a method for preparing the above block copolymer having fluorescence emission properties, comprising steps of:

performing a Michael reaction and a click reaction on a polymer B containing a sulfhydryl end group and a polymer C containing an azide group and a chemical conjugated molecule D, to obtain the block copolymer as shown in the Formula I-1;

wherein,
x is and
m is 23-445, and n is 10-150.

Preferably, in the above reaction process, the conjugation efficiency of the block copolymer is in-situ monitored by fluorescence emission intensity.

The present disclosure further provides a targeted drug having fluorescence emission properties, which is prepared by using the above conjugate as a bridging molecule, and has a structure as shown in Formula II-1:

Formula II-1 wherein,

Target is a targeted group, comprising cyclic RGD polypeptide, folic acid or sulfamide; and Drug is a drug group, comprising doxorubicin, camptothecin or paclitaxel.

The present disclosure further provides a method for preparing the targeted drug having fluorescence emission properties, comprising steps of:

performing a Michael reaction and a retro-D-A reaction on a targeted molecule F, a drug molecule G and a chemical conjugated molecule H, to obtain the targeted drug as shown in the Formula II-1;

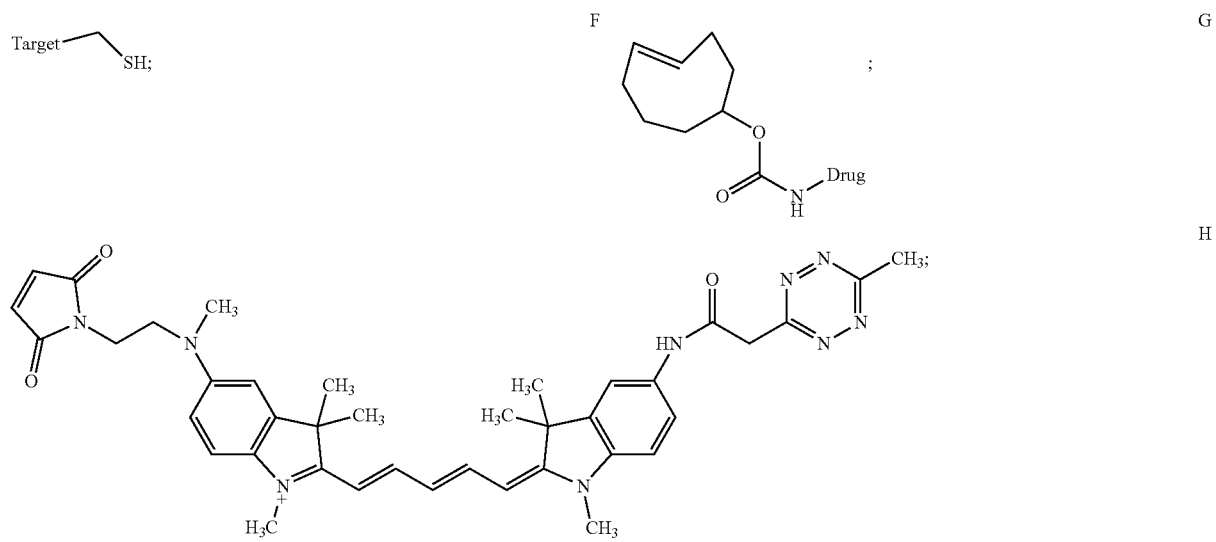

wherein,

Target is a targeted group, comprising cyclic RGD polypeptide, folic acid or sulfamide; and Drug is a drug group, comprising doxorubicin, camptothecin or paclitaxel.

Preferably, in the above reaction process, the conjugation efficiency of the drug molecule and the targeted molecule is in-situ monitored by infrared fluorescence emission intensity.

The present disclosure also provides use of the targeted drug in delivery of a targeted mediated drug.

The present disclosure provides an antibody-drug/probe conjugate having fluorescence emission properties, which comprises a structure as shown in Formula I-2:

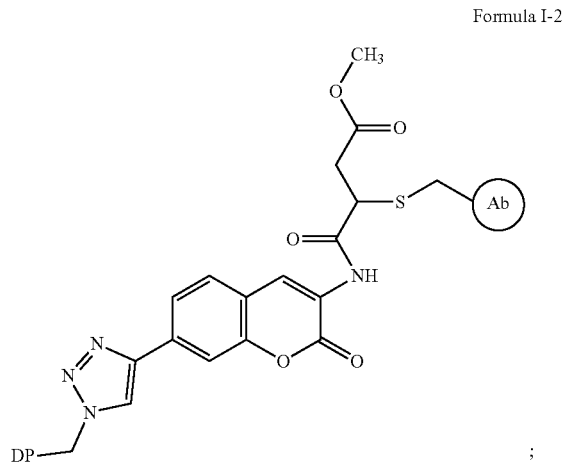

wherein, the Ab is an antibody, and DP is a fluorescence probe or a drug molecule.

The antibody-drug/probe conjugate provided in the present disclosure has a feature of self-reported conjugation efficiency, which bridges an antibody and a probe/drug molecule by a bifunctional fluorescent molecule. The bifunctional fluorescent molecule itself has no or only weak fluorescence emission capability, and only after the antibody-probe/drug is conjugated, the florescent molecule has strong fluorescence emission. Therefore, the conjugation process can be in-situ monitored by fluorescence monitoring, and the antibody-drug/probe conjugate can be applied to the delivery of therapeutic polypeptide and anti-cancer drugs.

Specifically, when DP is a fluorescent probe, the present disclosure further provides an antibody-probe conjugate having fluorescence emission properties, which has a structure as shown in Formula II-2:

Formula II-2

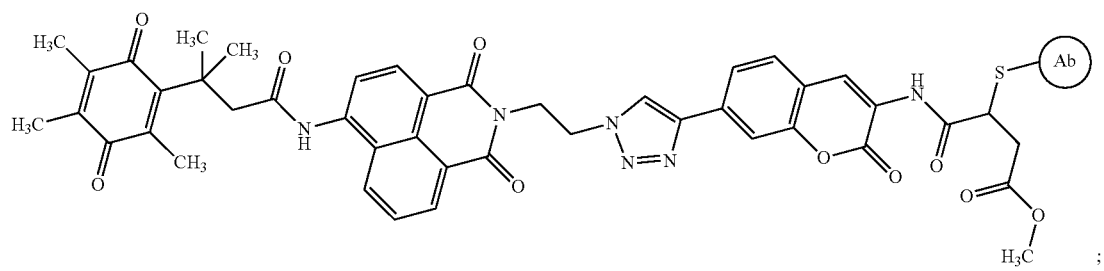

wherein Ab is a carcinoembryonic antigen monoclonal antibody or Herceptin.

The present disclosure further provides a method for preparing the antibody-probe conjugate, comprising steps of:

performing a Michael reaction and a click reaction on a monoclonal antibody, a fluorescence probe A containing an azide group and a bifunctional fluorescent molecule D, to obtain the antibody-probe conjugate as shown in Formula II-2.

The monoclonal antibody is a carcinoembryonic antigen monoclonal antibody or Herceptin containing a sulfhydryl group.

The fluorescence probe A containing an azide group is as shown in Formula A:

A

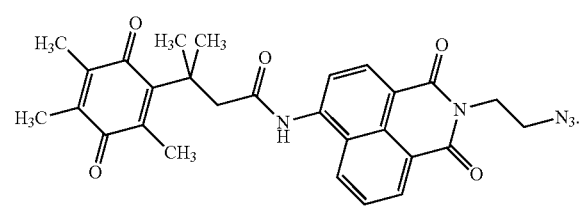

The bifunctional fluorescent molecule D is as shown in Formula D:

D

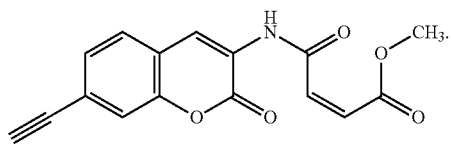

In the present disclosure, the raw material ratio and reaction conditions of the above reaction are not particularly limited, and may be a ratio and a condition of a Michael reaction and a click reaction which are conventional in the art.

Preferably, the conjugation efficiency of the antibody-probe conjugate is in-situ monitored by fluorescence emission intensity.

The above antibody-probe conjugate provided in the present disclosure has a fluorescence change under the action of quinone oxidoreductase, and thus can be used as a reaction indicator of an antigen and a quinone oxidoreductase.

When DP is a drug molecule, the present disclosure provides an antibody-drug conjugate having fluorescence emission properties, which has a structure as shown in Formula III:

Formula III

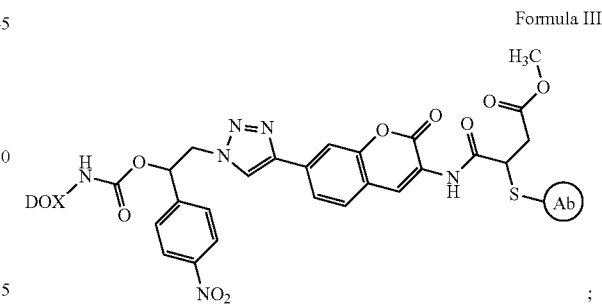

wherein, DOX is doxorubicin, and Ab is a carcinoembryonic antigen monoclonal antibody or Herceptin.

The present disclosure provides a method for preparing the above antibody-drug conjugate according, comprising steps of:

performing a Michael reaction and a click reaction on a monoclonal antibody, a prodrug molecule E containing an azide group and a bifunctional fluorescent molecule D, to obtain the antibody-drug conjugate as shown in Formula III;

the monoclonal antibody is a carcinoembryonic antigen monoclonal antibody or Herceptin containing a sulfhydryl group.

The prodrug molecule E containing an azide group is as shown in Formula E:

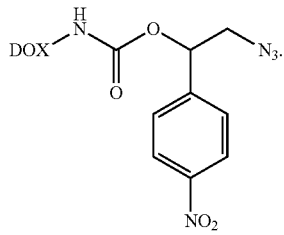

In Formula E, DOX is doxorubicin.

The amino group in Formula E is the amino group on the doxorubicin tetrahydropyran ring.

The bifunctional fluorescent molecule D is as shown in Formula D:

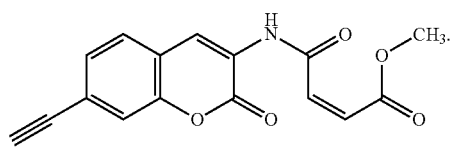

In the present disclosure, the raw material ratio and reaction conditions of the above reaction are not particularly limited, and may be a ratio and a condition of a Michael reaction and a click reaction which are conventional in the art.

In the present disclosure, preferably, the conjugation efficiency of the antibody-drug conjugate is in-situ monitored by fluorescence emission intensity.

The above antibody-drug conjugate provided in the present disclosure can release the pro-drug doxorubicin under the action of nitroreductase, and thus can be used as a fluorescent indicator in real-time monitoring drug release, or as a targeted drug release carrier.

The present disclosure provides a protein/polypeptide-polymer conjugate having fluorescence emission properties, which has a structure as shown in Formula I-3:

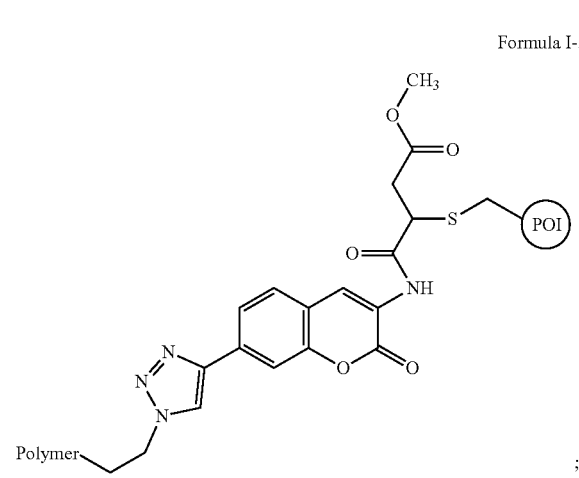

wherein, POI is a protein or a polypeptide; and Polymer is a polymer.

The protein/polypeptide-polymer conjugate bridges the protein/polypeptide and the polymer by a bifunctional fluorescent molecule. The bifunctional fluorescent molecule itself has no or only weak fluorescence emission capability, and only after the protein/polypeptide-polymer is conjugated, the florescent molecule has strong fluorescence emission. Therefore, the conjugation process of the protein/polypeptide-polymer conjugate can be in-situ monitored by fluorescence changes, and the protein/polypeptide-polymer conjugate can be applied to the delivery of therapeutic polypeptide and anti-cancer drugs.

In some embodiments of the present disclosure, POI is bovine serum albumin, and Polymer is polyethylene glycol, which has a structure as shown in Formula I-a:

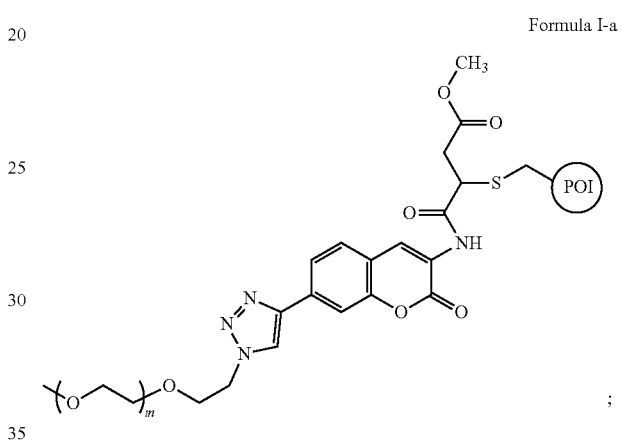

wherein m is 23-445.

The protein-polymer conjugate is preferably prepared by the following method:

performing a Michael reaction and a click reaction on a bovine serum albumin containing a sulfhydryl group, a polyethylene glycol containing an azide end group and compound D, to obtain a protein-polymer conjugate as shown in Formula I-a;

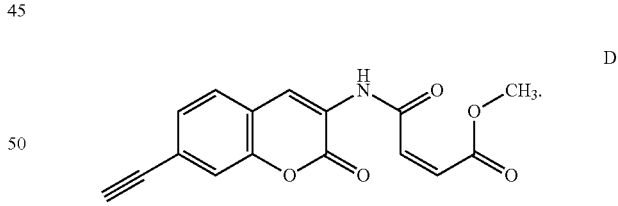

The polyethylene glycol containing an azide end group has a following structure:

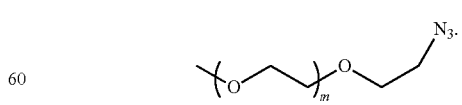

In the present disclosure, the raw material ratio and reaction conditions of the above reaction are not particularly limited, and may be a ratio and a condition of a Michael reaction and a click reaction which are conventional in the art.

In the present disclosure, preferably, the conjugation efficiency of the protein-polymer conjugate is in-situ monitored by fluorescence emission intensity.

In other embodiments of the present disclosure, POI is salcatonin, and Polymer is polyethylene glycol, which has a structure as shown in Formula I-a:

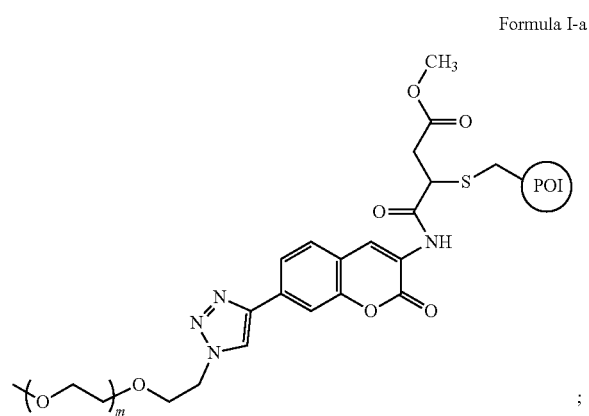

Formula I-a wherein, m is 23-445.

The above protein-polymer conjugate is preferably prepared by the following method:

performing a Michael reaction and a click reaction on salcatonin containing a sulfhydryl group, a polyethylene glycol containing an azide end group and a compound D, to obtain a protein-polymer conjugate as shown in Formula I-a.

The polyethylene glycol containing an azide end group and the compound D are the same as that above, which are not repeated herein.

In the present disclosure, the raw material ratio and reaction conditions of the above reaction are not particularly limited, and may be a ratio and a condition of a Michael reaction and a click reaction which are conventional in the art.

In the present disclosure, preferably, the conjugation efficiency of the protein-polymer conjugate is in-situ monitored by fluorescence emission intensity.

In other embodiments of the present disclosure, POI is a matrix metalloproteinase cleavable polypeptide, which has a sequence of βAPVGLIGβAC—SH, wherein SH is a sulfhydryl group (the sulfhydryl group is located at the carbon-end cysteine residue). The polypeptide is purchased from China Peptides Co. Ltd. Polymer is polytrimethylene carbonate, which has a structure as shown in Formula I-b:

The method preferably comprises steps of:

performing a Michael reaction and a click reaction on a matrix metalloproteinase cleavable polypeptide as shown in Formula J, a polytrimethylene carbonate containing an azide end group as shown in Formula K and compound D, to obtain the peptide-polymer conjugate as shown in Formula I-b;

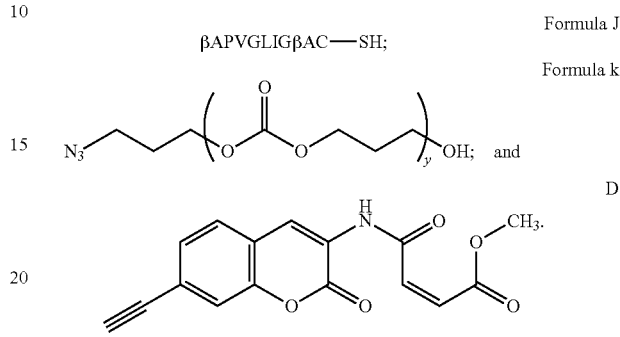

Formula J

βAPVGLIGβAC—SH;

Formula k and

D

In the present disclosure, the raw material ratio and reaction conditions of the above reaction are not particularly limited, which may be a ratio and a condition of a Michael reaction and a click reaction which are conventional in the art.

In the present disclosure, preferably, the conjugation efficiency of the protein-polymer conjugate is in-situ monitored by fluorescence emission intensity.

The present disclosure further discloses a vesicle consisting of the above polypeptide-polymer conjugate or the polypeptide-polymer conjugate prepared by the above method.

In the present disclosure, the method for preparing the vesicle is not particularly limited, which may be the method well-known to one of ordinary skill in the art. In the present disclosure, preferably, the above polypeptide-polymer conjugate is dissolved in DMSO, added with deionized water, and dialyzed with deionized water.

The polymer vesicles provided by the present disclosure have uniform dispersion and uniform particle size distribution, and the particle size distribution thereof is 60-150 nm.

The above polymer vesicle has a property of matrix metalloproteinase response, and thus can be used as a drug carrier, or as a fluorescent indicator in real-time monitoring drug release.

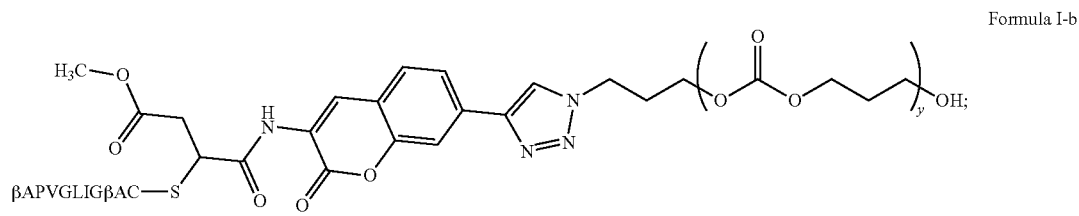

Formula I-b wherein, y is 10-55.

In order to further illustrate the present disclosure, the conjugate containing a fluorescent chromophore, the block copolymer, the antibody-drug/probe conjugate, the protein/polypeptide-polymer conjugate, the targeted drug provided by the present disclosure, the preparation method and the use thereof will be described in detail below in conjunction with the embodiments.

Preparation of Dicapped Coumarin (C1-C3)

The synthetic rout is as follows:

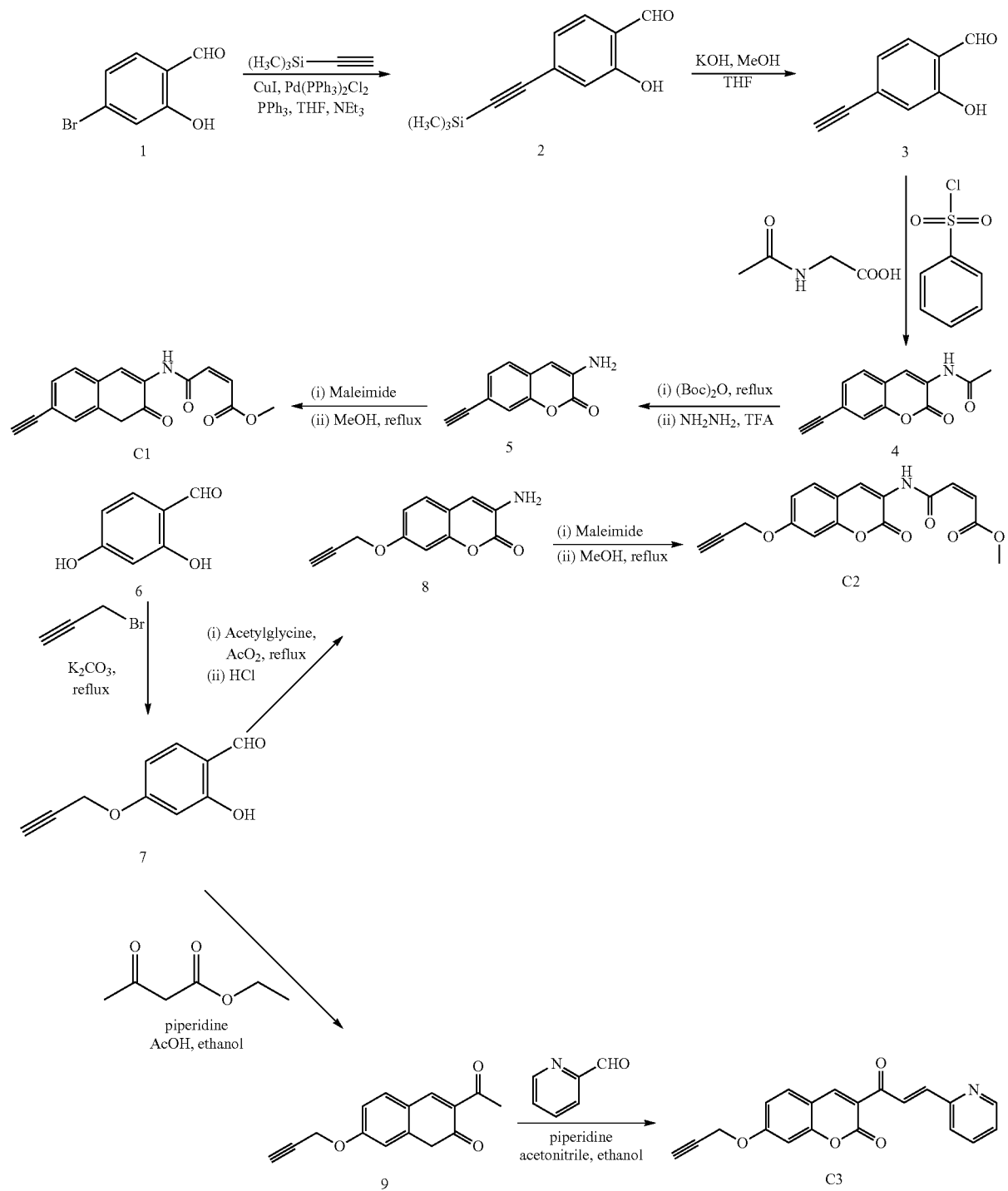

Example 1 Synthesis of C1

4-bromosalicylaldehyde (1; 3.11 g, 15.4 mmol), Pd(PPh$_3$)$_2$Cl$_2$ (0.22 g, 0.31 mmol), PPh$_3$ (0.061 g, 0.23 mmol) and anhydrous tetrahydrofuran (50 mL) were added into a reaction flask containing a magnetic stirrer bar. Dry nitrogen was used to bubble up the reaction system to degassing for 30 min. The newly-distilled dry Et$_3$N (3.05 g, 30.0 mmol) and trimethylsilylacetylene (1.67 g, 17.0 mmol) were added in nitrogen atmosphere, and the solution turned orange. After stirring for 20 min, the promotor CuI (0.088 g, 0.46 mmol) was added in the reaction system in nitrogen atmosphere, and the solution turned dark brown. The reaction system was stirred at room temperature overnight, and then the solvent was removed to obtain a dark brown solid. The solid was dissolved in n-pentane and filtered, to obtain a yellow solution. All the solvent was removed by rotary evaporation. Finally, the resultant was recrystallized for twice in n-hexane to obtain a yellow crystal 2 (2.96 g, yield: 88.2%, >95% HPLC pure).

$^1$H NMR (CDCl$_3$, δ, ppm, TMS): 11.0 (s, 1H, benzene-OH), 9.87 (s, 1H, —CHO), 7.48 (d, J=8.4 Hz, 1H, aromatic hydrogen), 7.07 (m, 2H, aromatic hydrogen), 0.26 (s, 9H, —Si(CH$_3$)$_3$)$_o$ The 2 (2.85 g, 13.1 mmol) was dissolved in dry THF (40 mL), and then 20 mL MeOH solution containing KOH (0.74 g, 13.2 mmol) was added in. The reaction system was stirred overnight at room temperature, and all the solvent was removed by rotary evaporation. The residue was dispersed again in water, and 1 mL acetic acid was added in. The mixture was extracted with 3×200 mL chloroform. The organic phases were combined, dried with anhydrous magnesium sulfate, and filtered to remove all the solvent to obtain a brown solid. The solid was recrystallized twice in n-hexane to obtain a yellow solid 3 (1.02 g, yield: 53.2%, >95% HPLC pure).

$^1$H NMR (CDCl$_3$, δ, ppm, TMS): 11.0 (s, 1H, benzene-OH), 9.89 (s, 1H, —CHO), 7.52 (d, J=8.4 Hz, 1H, aromatic hydrogen), 7.12 (m, 2H, aromatic hydrogen), 3.29 (s, 1H, —C≡CH)$_o$ The benzenesulfonyl chloride (2.51 g, 14.3 mmol), Et$_3$N (2.15 g, 21.3 mmol) and N-acetylglycine (0.88 g, 7.5 mmol) were dissolved in THF, and stirred overnight at room temperature. After removing the insoluble salts, the compound 3 (1.02 g, 7.0 mmol) was added in the reaction system and stirred at 80° C. for 10 h. The reaction system was then cooled to 0° C., to give a precipitation 4 (1.09 g, yield: 68.5%, >95% pure).

$^1$H NMR (CDCl$_3$, δ, ppm, TMS): 9.80 (s, 1H, —CO—NH—), 8.57 (s, 1H, aromatic hydrogen), 7.67 (d, J=8.4 Hz, 1H, aromatic hydrogen), 7.35 (m, 2H, aromatic hydrogen), 4.40 (s, 1H, —C≡CH), 2.14 (s, 3H, —COCH$_3$)$_o$ The compound 4 (1.09 g, 4.8 mmol), DMAP (0.11 g, 0.96 mmol) and (Boc)$_2$O (2.11 g, 9.8 mmol) were dissolved in 40 mL THF, and the reaction system was stirred at 70° C. for 4 h, and then cooled to room temperature. MeOH (10 mL) and NH$_2$NH$_2$.H$_2$O (0.96 g, 19.2 mmol) were added in, and the reaction system was further stirred for 4 h. CH$_2$Cl$_2$ was added in, and the reaction mixture was washed with 1 M HCl solution. The organic phase was collected and dried with anhydrous MgSO$_4$. The insoluble MgSO$_4$ was removed by filtration. All the solvent was all removed by rotary evaporation. The residue was dissolved in a mixed solvent of CH$_2$Cl$_2$ (40 mL) and TFA (10 mL), stirred for 2 h, and washed with NaHCO$_3$ solution. The organic phase was dried with MgSO$_4$. After removing MgSO$_4$ by filtration, the solvent was removed by rotary evaporation to give the product 5 (0.76 g), which was immediately used for synthesizing C1. The specific processes were shown below:

The compound 5 (0.76 g, 4.1 mmol) and maleic anhydride (2.01 g, 20.5 mmol) were dissolved in 100 mL acetone, refluxed overnight, and cooled to 0° C. to give a yellow solid precipitation. The above yellow solid precipitation (1.03 g) and p-toluenesulfonic acid monohydrate (154 mg) were dissolved in 30 mL methanol, refluxed overnight, and cooled to 0° C. to give a crude product yellow precipitation. The crude product was purified by column chromatography using EtOAc/DCM (v/v=½) as the eluent, to give a yellow solid C1 (480 mg, yield: 39.4%, >95% HPLC pure).

$^1$H NMR (d$_6$-DMSO, δ, ppm, TMS): 10.28 (s, 1H, —CONH—), 8.65 (s, 1H, aromatic hydrogen), 7.73 (d, J=8.1 Hz, 1H, aromatic hydrogen), 7.49 (s, 1H, aromatic hydrogen), 7.38 (s, 1H, aromatic hydrogen), 6.74 (d, J=9.3 Hz, 1H, —NHCOCH═CH—), 6.51 (d, J=8.7 Hz, 1H, —CH═CH—COO—), 4.43 (s, 1H, —C≡CH), 3.66 (s, 3H, —COO—CH$_3$), and the hydrogen nuclear magnetic resonance spectroscopy of it was shown in FIG. 1.

Figure 2:
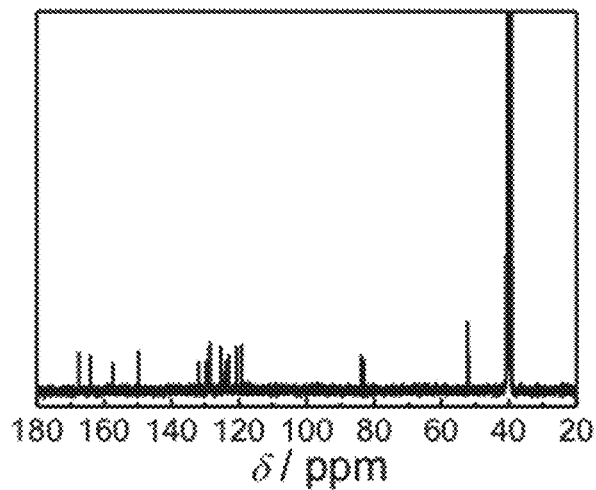
FIG. 2 shows the carbon nuclear magnetic resonance spectroscopy of C1 prepared in the present disclosure.

$^{13}$C NMR (CDCl$_3$, δ, ppm TMS): 167.5, 164.2, 157.6, 149.9, 131.9, 129.7, 128.8, 128.6, 125.3, 124.0, 123.1, 120.7, 119.2, 83.8, 83.0, 52.1, and the carbon nuclear magnetic resonance spectroscopy of it was shown in FIG. 2.

RP-HPLC analysis: 4.4 min (mobile phase: MeOH/H$_2$O v/v 4/1).

Figure 3:
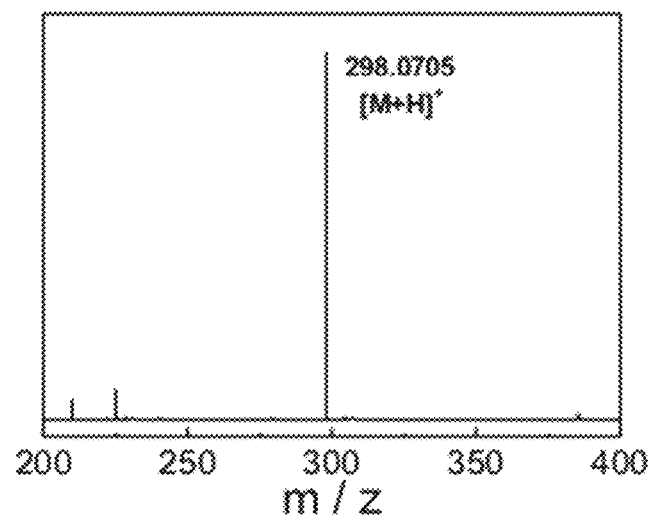
FIG. 3 shows the electrospray mass spectrometry of C1 prepared in the present disclosure.

ESI-MS: m/z calc. for C$_{16}$H$_{12}$NO$_5$: 298.06 [M+H]$^+$; found: 298.0705, and the electrospray mass spectrometry was shown in FIG. 3.

Figure 4:
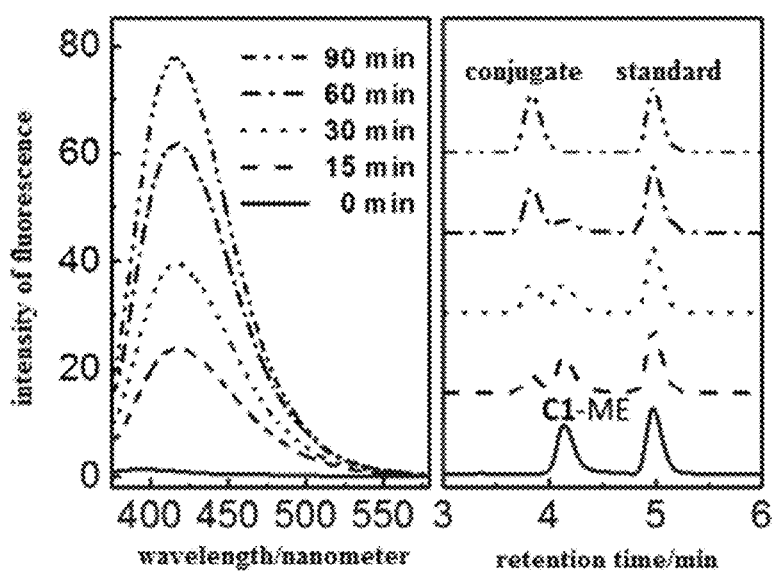
FIG. 4 shows the fluorescence change and high performance liquid chromatography curve during the preparation of C1 in the present disclosure.
Figure 5:
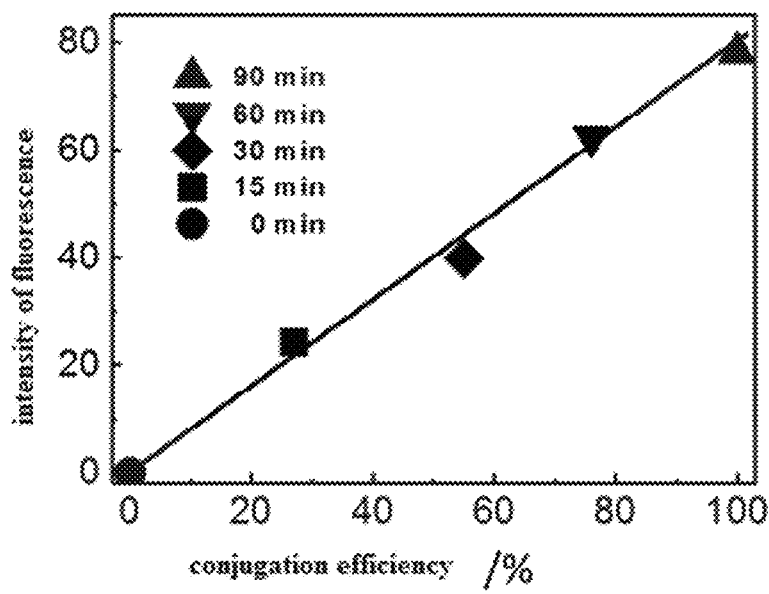
FIG. 5 shows the fluorescence change and conjugation efficiency curve during the preparation of C1 in the present disclosure.

In the reaction process, the conjugation efficiency of the block copolymer was monitored by fluorescence emission intensity, and the results were shown in FIG. 4 and FIG. 5, wherein FIG. 4 shows the fluorescence change and high performance liquid chromatography curve in the reaction process; and FIG. 5 shows the curve of relationship between the fluorescence change and conjugation efficiency.

Example 2 Synthesis of C2

2,4-Dihydroxybenzaldehyde (6, 10.0 g, 72.4 mmol), propargyl bromide (8.33 g, 70.0 mmol), and K$_2$CO$_3$ (19.35 g, 140.0 mmol) were added in 100 mL acetone, refluxed overnight, and recovered to room temperature. The resultant was filtered, and all the solvent was removed. The residue was dissolved in CH$_2$Cl$_2$, and washed with water. The organic phase was collected, dried with MgSO$_4$, filtered, and subjected to rotary evaporation. The crude product was further purified by column chromatography using EtOAc/PE (v/v=1:2) as an eluent, to obtain a white powder 7 (3.2 g, yield: 25.9%, >95% HPLC pure).

$^1$H NMR (CDCl$_3$, δ, ppm, TMS): 11.45 (s, 1H, benzene-OH), 9.75 (s, 1H, —CHO), 7.46 (d, J=8.1 Hz, 1H, aromatic hydrogen), 6.61 (d, J=8.1 Hz, 1H, aromatic hydrogen), 6.53 (s, 1H, aromatic hydrogen), 4.75 (s, 2H, —OCH$_2$C≡CH), 2.58 (s, 1H, —OCH2≡CH).

N-acetylglycine (2.23 g, 19.1 mmol), anhydrous sodium acetate (4.48 g, 54.6 mmol), and compound 7 (3.21 g, 18.2 mmol) was added in 100 mL dry acetic anhydride. The reaction system was stirred at 150° C. for 12 h, cooled to room temperature, and poured to ice water (300 mL) to obtain a yellow precipitation. The yellow solid was separated by filtration, and refluxed in a mixed solution of concentrated hydrochloric acid and ethanol (v:v=2:1) for 2 h. The reaction system was then poured into ice water (100 mL), and the pH was adjusted to 5-6 by NaOH solution, and the system was concentrated to about 30 mL to obtain a precipitation of the crude product. Finally, the crude product was recrystallized for twice in ethanol to give the product 8 (3.49 g, purity: 89.2%, >95% HPLC pure).

¹H NMR (d₆-DMSO, δ, ppm, TMS): 10.22 (s, 1H, —CONH—), 8.67 (s, 1H, aromatic hydrogen), 7.69 (d, J=8.4 Hz, 1H, aromatic hydrogen), 7.03 (m, 2H, aromatic hydrogen), 6.63 (d, J=9.3 Hz, 1H, —COCH═CH—), 6.42 (d, J=9.0 Hz, 1H, —CH═CHCOOH), 4.92 (s, 1H, —OCH₂C≡CH), 2.50 (m, 1H, —OCH₂C≡CH).

The compound 8 (2.15 g, 10.0 mmol) and maleic anhydride (2.01 g, 20.5 mmol) were dissolved in CHCl₃ (50 mL), refluxed for 6 h, and cooled to 0° C. to give a yellow solid (2.76 g). The yellow solid and P-toluenesulfonic acid monohydrate (190 mg) were dissolved in 200 mL methanol, refluxed overnight, and cooled to 0° C. to give a precipitation of crude product. The crude product was further purified by column chromatography using EtOAc/DCM (v/v=⅓) as an eluent, to give a yellow solid C2 (1.81 g, purity: 55.4%, >95% HPLC pure).

¹H NMR (CDCl₃, δ, ppm, TMS): 9.98 (s, 1H, —CONH—), 8.75 (s, 1H, aromatic hydrogen), 7.41 (d, J=8.4 Hz, 1H, aromatic hydrogen), 6.93 (m, 2H, aromatic hydrogen), 6.41 (d, J=9.3 Hz, 1H, —COCH═CH—), 6.25 (d, J=9.0 Hz, 1H, —CH═CHCO—), 4.74 (d, 2H, —OCH₂C≡CH), 3.85 (s, 3H, —COOCH₃), 2.55 (m, 1H, —OCH2C≡CH).

¹³C NMR (d₆-DMSO, δ, ppm TMS): 167.7, 163.8, 159.3, 157.9, 151.8, 131.7, 129.8, 129.6, 126.0, 122.2, 113.8, 113.6, 102.1, 79.4, 79.0, 56.5, 52.2.

ESI-MS: m/z calc. for C₁₇H₁₄NO₆: 328.07 [M+H]⁺, C₁₇H₁₃NO₆Na: 350.08 [M+Na]⁺; and the theoretical values were particularly: 328.081, and 350.0916₀

Example 3 Synthesis of C3

Ethyl acetoacetate (3.19 g, 24.5 mmol), compound 7 (3.52 g, 20.0 mmol), piperidine catalyst (0.1 g) and acetic acid (0.1 mL) were added in 15 mL anhydrous ethanol. The reaction mixture was refluxed for 12 h, and cooled to room temperature to give a bright yellow precipitation crude product. The crude product was recrystallized in anhydrous ethanol to give a bright yellow crystal 9 (3.12 g, yield: 64.5%, >95% HPLC pure).

¹H NMR (CDCl₃, δ, ppm, TMS): 8.49 (s, 1H, aromatic hydrogen), 7.57 (d, J=8.1 Hz, 1H, aromatic hydrogen), 6.97 (m, 2H, aromatic hydrogen), 4.80 (s, 2H, —OCH₂C≡CH), 2.71 (s, 3H, —COCH₃), 2.61 (t, 1H, —OCH2C≡CH).

The compound 9 (2.25 g, 9.3 mmol) and 2-pyridylaldehyde (2.21 g, 20.6 mmol) were dissolved in EtOH/CH₃CN (80 mL, 1:1 v/v), and 0.4 g piperidine was added in as the catalyst. After the reaction mixture was refluxed for 24 h in nitrogen atmosphere, the solvent was removed by rotary evaporation. The crude product was recrystallized for several times in anhydrous ethanol to give a yellow solid C3 (1.25 g, yield: 40.6%, >95% HPLC pure).

¹H NMR (CDCl3, δ, ppm, TMS): 8.68 (d, J=7.8 Hz, 1H, aromatic hydrogen), 8.56 (s, 1H, aromatic hydrogen), 8.30 (d, J=9.0 Hz, 1H, —COCH═CH—), 7.80 (d, J=9.3 Hz, 1H, —COCH═CH—), 7.70 (m, 1H, aromatic hydrogen), 7.59 (m, 2H, aromatic hydrogen), 7.28 (m, 1H, aromatic hydrogen), 6.97 (m, 2 H, aromatic hydrogen), 4.80 (s, 2H, —OCH₂C≡CH), 2.61 (t, 1H, —OCH₂C≡CH).

¹³C NMR (CDCl3, δ, ppm TMS): 186.8, 162.9, 159.3, 157.5, 153.5, 150.3, 148.3, 143.1, 136.7, 131.4, 127.8, 124.6, 124.3, 121.9, 114.3, 112.8, 101.7, 56.4.

ESI-MS: m/z calc. for C₂₀H₁₄NO4: 332.09 [M+H]⁺; found: 332.0911.

Example 4 Synthesis of HS-PDMA₃₈

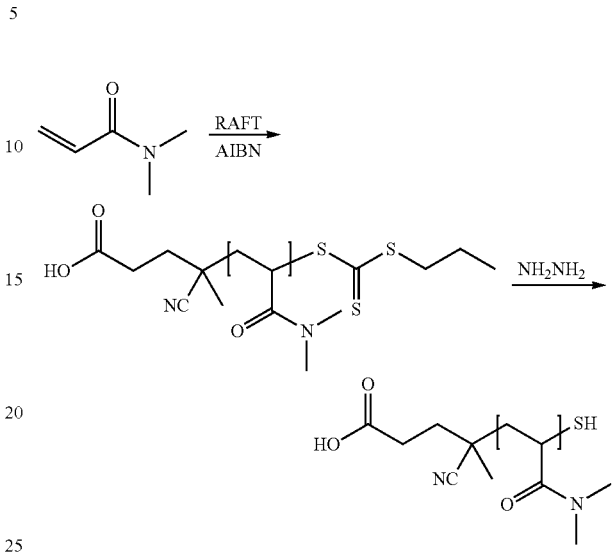

Charged dimethyl acrylamide (DMA) (2.0 g, 20.2 mmol), 4-cyano-4-(propylthiocarbonothioylthio)pentanoic acid (223 mg, 0.8 mmol), 2,2'-diazoisobutyronitrile (AIBN) (16 mg, 0.98 mmol) and dioxane (4 ml) were added in a sealing tube containing a stirring bar. The sealing tube was degassed for three times by a freezing-pumping-unfreezing operation, then sealed in vacuum, and reacted at 70° C. in a constant temperature oil bath pan for 6 h. The reaction was quenched with liquid nitrogen. The sealing tube was unsealed. The reaction mixture was diluted with THF, and precipitated for three times in excess diethyl ether. The product was dried in a vacuum drying oven to give a yellow powder PDMA (1.63 g, 86% yield).

¹H NMR (CDCl3, δ, ppm, TMS: 2.8-3.2 (N(CH₃)₂), 1.1-2.8 (main chain), 1.0 (—S—CH₂—).

The actual degree of polymerization of PDMA block was 38 determined by ¹HNMR, and so the product was abbreviated as PDMA₃₈.

PDMA₃₈ (500 mg, 0.22 mmol) was dissolved in dry CH₂Cl₂. 2 h after adding NH₂NH₂·H₂O (55 mg, 1.1 mmol) dropwise into the reaction tube, the solution was concentrated and precipitated for three times with excess ethyl ester. The resultant was dried in vacuum drying oven to give white powder HS-PDMA₃₈ (420 mg, yield 93.8%).

Example 5 Fluorescence Conjugate of HS-PDMA₃₈ and PEG₄₅-N₃ Mediated by C1

HS-PDMA₃₈ (35 mg, 17.5 μmol), PEG₄₅-N₃ (350 mg, 175 μmol) and PEG₂₂₇ (external standard, 300 mg) were dissolved in deionized water (45 mL, pH 7.0), then C1 (5.2 mg, 17.5 μmol, dissolved in 5 mL DMSO) and CuSO₄/vitamin C (1/5 mole ratio) were added in. The reaction system was stirred at 25° C. for different times. After a given time, about 1.0 mL of the reaction solution was sampled, and diluted in 9.0 mL THF. Copper ion adsorption resin (American Ocean Chemical Company, 200 mg) was quickly added in to remove the copper ions. The resultant was then vibrated for 5 min. The supernatant was filtered out with a 0.22 μm sterile syringe injector followed by further fluorescence and GPC test.

Figure 6:
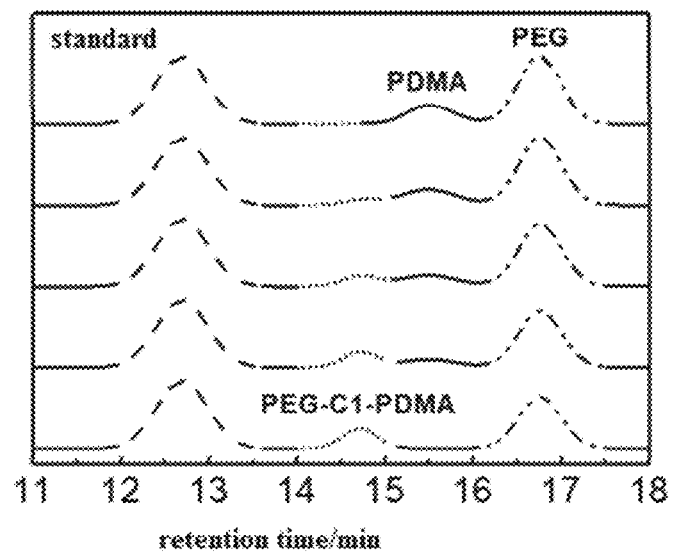
FIG. 6 shows the gel permeation chromatography of the block polymer prepared in Example 5 of the present disclosure.
Figure 7:
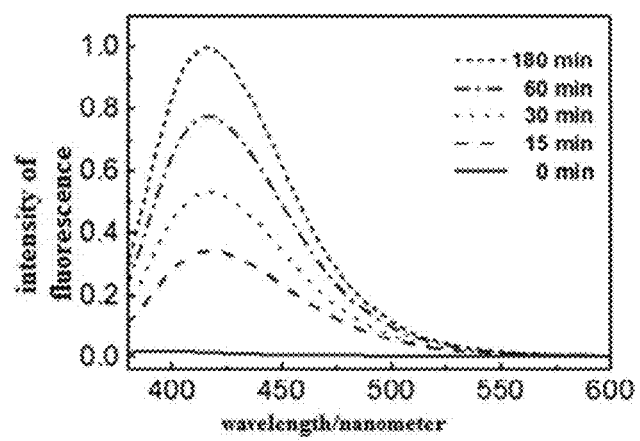
FIG. 7 shows the fluorescence change during the reaction of preparing the block polymer in Example 5 of the present disclosure.
Figure 8:
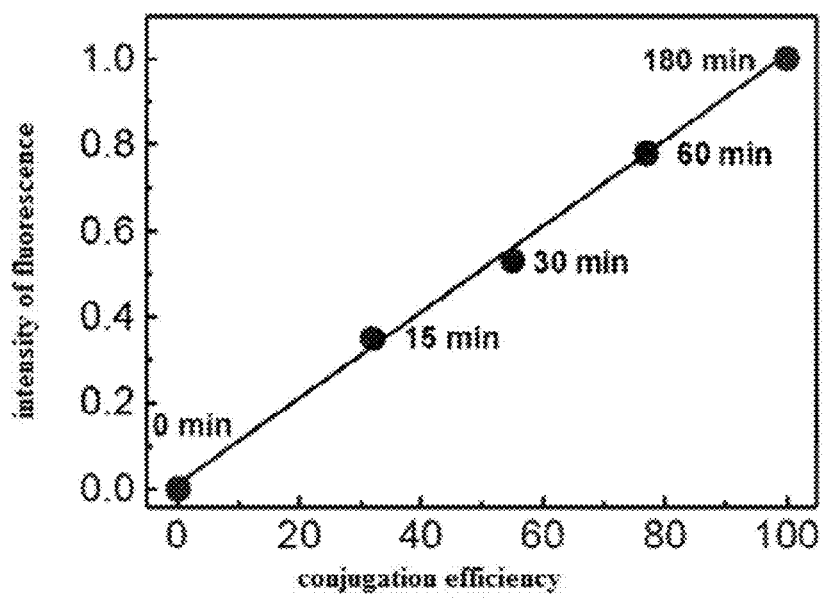
FIG. 8 shows the relationship between fluorescence change and conjugation efficiency during the conjugation of a block polymer in Example 5 of the present disclosure.

The conjugation efficiency of the block copolymer was monitored by fluorescence emission intensity, and the results were shown in FIG. 6-FIG. 8, wherein FIG. 6 was gel permeation chromatograph, and FIG. 7 showed the fluorescence change curve in the reaction process, and FIG. 8 was the curve of relationship between the fluorescence change and the conjugation efficiency in the reaction process.

It can be concluded from FIG. 6-8 that the fluorescence increase of fluorescent chromophore had a linear correlation with the conjugation efficiency of the block copolymer. Therefore, the conjugation efficiency of the block polymer was tested by in-situ real-time monitoring the fluorescence change.

In view of the examples above, the conjugation efficiency of the polymer was in-situ monitored by infrared fluorescence emission intensity in the present disclosure.

Example 6 Synthesis of C1 Mediated Targeted Medicine

The synthesis route was as follows:

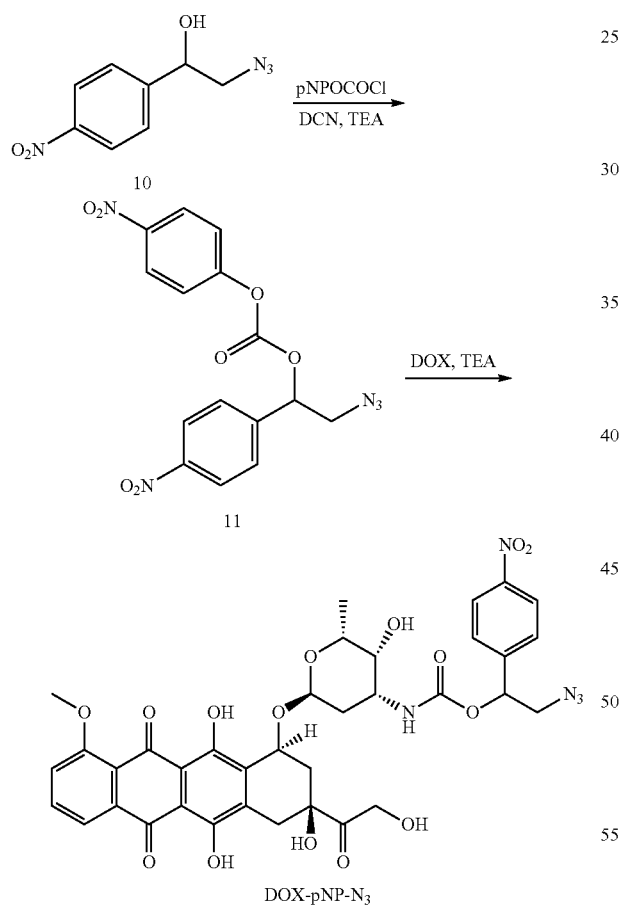

The compound 10 (4.16 g, 20.0 mmol) and NEt$_3$ (3.22 g, 31.9 mmol) were added in 100 mL dry DCM, and cooled to 0° C. 4-Nitrochloroformic acid phenolate (6.12 g, 30.4 mmol, 20 mL DCM solution) was added dropwise in, and reacted at 0° C. for 12 h. After filtration, the solution was washed with water. The organic phase was dried with anhydrous MgSO$_4$. After MgSO$_4$ was filtered out, the resultant was subjected to rotary evaporation to give a crude product. The resultant was further purified by column chromatography using EtOAc/PE (v/v=1:8) as an eluent, to give a white powder 11 (3.82 g, yield: 51.2%, purity>95%, HPLC pure).

$^1$H NMR (CDCl$_3$, δ, ppm, TMS): 8.29 (t, 4H, aromatic hydrogen), 7.64 (d, 2H, aromatic hydrogen), 7.38 (d, 2H, aromatic hydrogen), 5.74 (m, 1H, >CH—CH$_2$N$_3$), 3.5-3.8 (m, 2H, >CH—CH$_2$N$_3$).

The compound 11 (186 mg, 0.5 mmol), DOX-HCl (58 mg, 0.1 mmol) and NEt$_3$ (120 mg, 1.18 mmol) were dissolved in dry DMF (10 mL), and stirred at room temperature for 24 h. After removing the salt by suction filtration, the solvent was removed by rotary evaporation to give the crude product. The crude product was further purified by column chromatography using CHCl$_3$/MeOH (v/v=100:0 to 90:10) as an eluent, to give a red powder DOX-pNB-N$_3$ (43 mg, yield: 55.3%, purity>95%).

Figure 9:
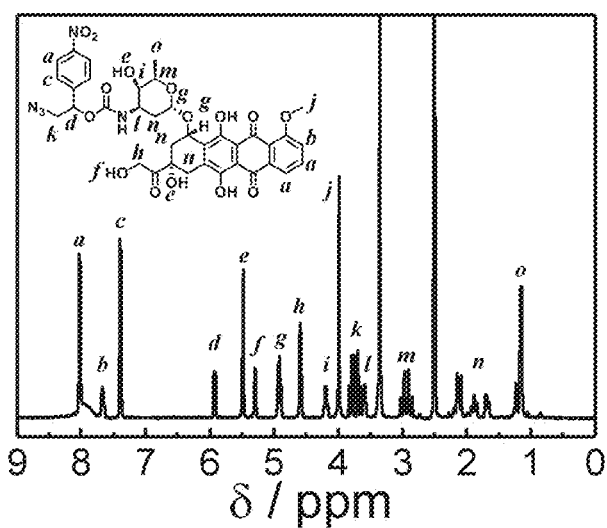
FIG. 9 shows the hydrogen nuclear magnetic resonance spectroscopy of the pro-drug molecules prepared in Example 6.

$^1$H NMR (DMSO-d$_6$, δ, ppm): 7.6-8.2 (broad, 5H, aromatic hydrogen), 7.42 (d, 2H, aromatic hydrogen), 5.95 (m, 1H, >CH—CH$_2$N$_3$), 5.49 (d, 2H, >CH—OH& C—OH), 5.31 (s, 1H, —CH$_2$OH), 4.92 (m, 2H, >CH—O—CH<), 4.62 (d, 2H, —CH$_2$OH), 4.15 (m, 1H, >CH—OH), 3.95 (s, 3H, —OCH$_3$), 3.5-3.9 (m, 3H, >CH—CH$_2$N$_3$&>CH—NHCO—), 2.8-3.1 (m, 1H, >CHCH$_3$), 1.6-2.2 (m, 4H, —CH$_2$—), 1.12 (d, 3H, >CHCH$_3$). Its hydrogen magnetic resonance spectroscopy was shown in FIG. 9.

RP-HPLC analysis: 3.7 min (eluent: MeOH/H$_2$O v/v ⅓).

Figure 10:
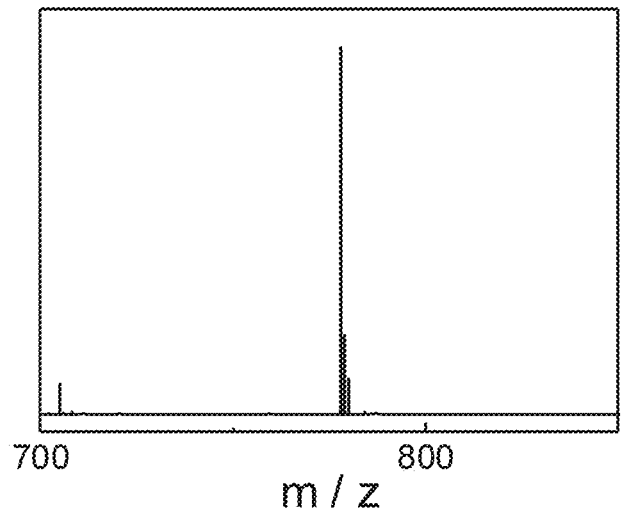
FIG. 10 shows the electrospray mass spectrometry of the pro-drug molecules prepared in Example 6.

ESI-MS: m/z calc. for C$_{36}$H$_{36}$N$_5$O$_{15}$: 778.21 [M+H]$^+$; found: 778.2109. Its electrospray mass spectrum was shown in FIG. 10.

200 μL C1 in DMSO (containing 0.2 μmol C1), DOX-pNB-N$_3$ (10.0 mg, 1.0 μmol) and CuSO$_4$/Na-ascorbate (1/5 molar ratio) were added in HS-cRGD (0.1 μmol, dissolved in 1.8 mL PBS buffer solution), stirred at 25° C. for different times. The conjugation progress was tested by in-situ monitoring the change of fluorescence emission at ~420 nm. 4 h later, copper ion adsorption resin (American Ocean Chemical Company, 100 mg) was quickly added in to remove the copper ions. After vibrating for 5 min, the supernatant was filtered out with a 0.22 μm sterile syringe injector.

The experimental results showed that the fluorescence increase of fluorescent chromophore had a linear correlation with the conjugation efficiency of the targeted drug. Therefore, the conjugation efficiency of targeted drug was tested by in-situ real-time monitoring the fluorescence change.

Example 7 Synthesis of Fluorescence Probe a (QNAM-N$_3$)

The synthesis route was as follows:

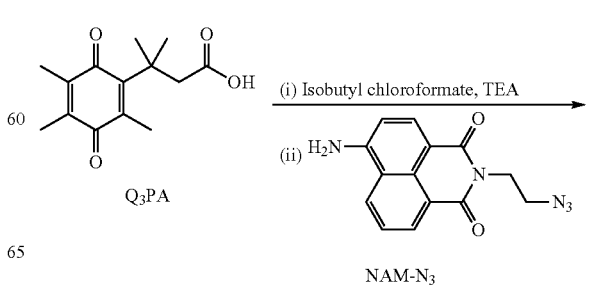

-continued

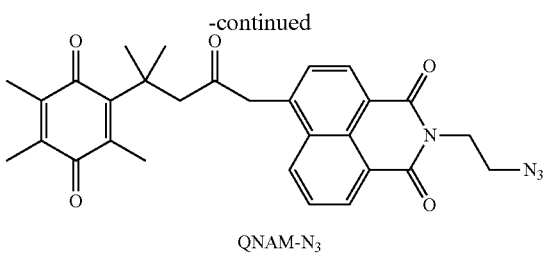

QNAM-N₃

Q₃PA (0.51 g, 2.0 mmol) and triethylamine (0.61 g, 6.0 mmol) were dissolved in 60 mL dichloromethane, and the mixture was cooled to 0° C. Then isobutyl chloroformate (0.31 g, 2.2 mmol) was added dropwise in slowly. After reacting for 1 h, NAM-N₃ (0.49 g, 1.75 mmol) was added in. The reaction system continuously reacted at 0° C. for 5 h. After the reaction completed, all the inorganic salt was removed by suction filtration, and all the solvent was removed by rotary evaporation to give a crude product. A pure product was obtained by column chromatography (ethyl acetate/n-hexane (v/v=⅕) was used as the mobile phase).

Figure 11:
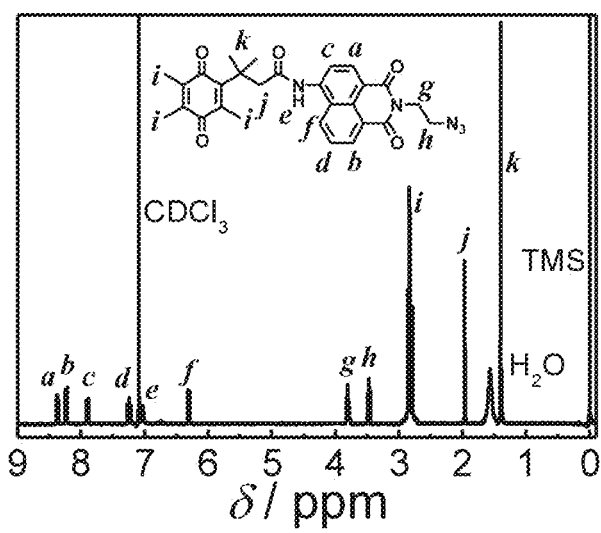
FIG. 11 shows the hydrogen nuclear magnetic resonance spectroscopy of the fluorescence probe A prepared in Example 7.

$^1$H NMR (CDCl₃, δ, ppm): 8.37 (d, 1H, aromatic hydrogen), 8.22 (d, 1H, aromatic hydrogen), 7.92 (d, 1H, aromatic hydrogen), 7.24 (t, 1H, aromatic hydrogen), 7.04 (broad, 1H, —CONH—), 6.29 (d, 1H, aromatic hydrogen), 3.81 (t, 2H, —CH₂—CH₂N₃), 3.47 (t, 2H, —CH₂N₃), 2.82 (m, 9H, quinone-(CH₃)₃), 1.95 (s, 2H, —CH₂—CONH—), 1.38 (s, 6H, >C(CH₃)₂). Its hydrogen magnetic resonance spectroscopy was shown in FIG. 11.

RP-HPLC analysis: 10.7 min (mobile phase: MeOH/H₂O v/v 7/3).

Figure 12:
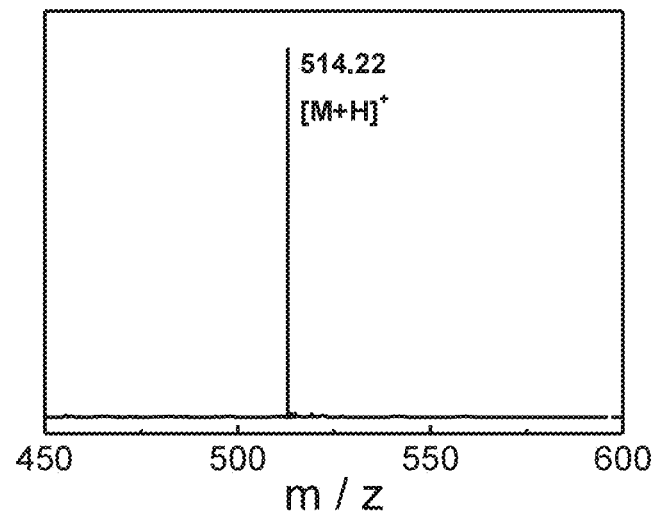
FIG. 12 shows the electrospray mass spectrometry of the fluorescence probe A prepared in Example 7.

ESI-MS: m/z calc. for C₂₈H₂₈N₅O₅: 514.20 [M+H]⁺; found: 514.22. Its electrospray mass spectrometry was shown in FIG. 12.

Example 8 Fluorescence Conjugate of Anti-Cea Antibody and DOX-pNB-N₃ or QNAM-N₃ Mediated by Bifunctional Fluorescent Molecule C1

Dithiothreitol (DTT, 154 mg, 100 μmol) was dissolved in phosphate buffer (PBS) (10 mL, pH 8.0, 50 mM), and 10 μL of the above solution (containing 0.1 μmol DTT) was added in a PBS (1 mL, pH 8.0, 50 mM) solution containing anti-CEA antibody (ACEA, 1 mg), and stirred at 37° C. for 30 min. The product was purified by ultrafiltration (Amicon Ultra-0.5, Millipore, molecular weight cut-off 10 kDa), and the product was redissolved again in the PBS (2.0 mg/mL, pH 7.0, 50 mM) before use. 5,5'-Dithiobis(2-nitrobenzoic acid) (DNTB) was used as a probe to determine the content of sulfhydryl group, and the number of sulfhydryl group in each antibody molecule was about 4.

10 μL DMSO solution of bifunctional fluorescent molecule C1 (0.5 μmol C1), 10 μL DOX-pNB-N₃ (0.5 μmol) or QNAM-N₃ solution (0.5 μmol) and CuSO₄/Na-ascorbate (1/5 molar ratio) were added in ACEA solution (0.2 mg, in 180 μL PBS, pH 7.0). The temperature was kept at 25° C., and the conjugation progress was in-situ monitored by fluorescence. After co-culturing for 6 h, the conjugate was further purified by ultrafiltration (Amicon Ultra-0.5, Millipore, molecular weight cut-off 10 kDa), to give an antibody-probe conjugate or an antibody-drug conjugate.

Figure 13:
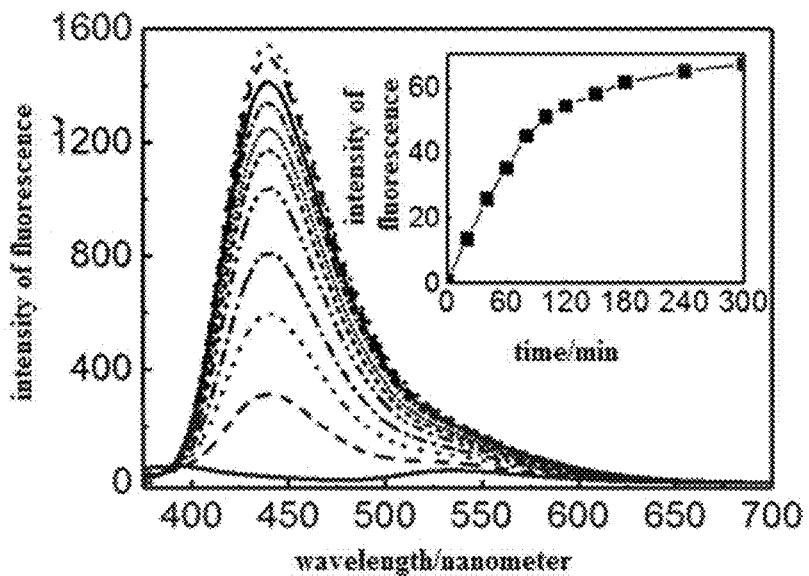
FIG. 13 shows the fluorescence change curve during the reaction of preparing the antibody-probe conjugate in Example 8.
Figure 14:
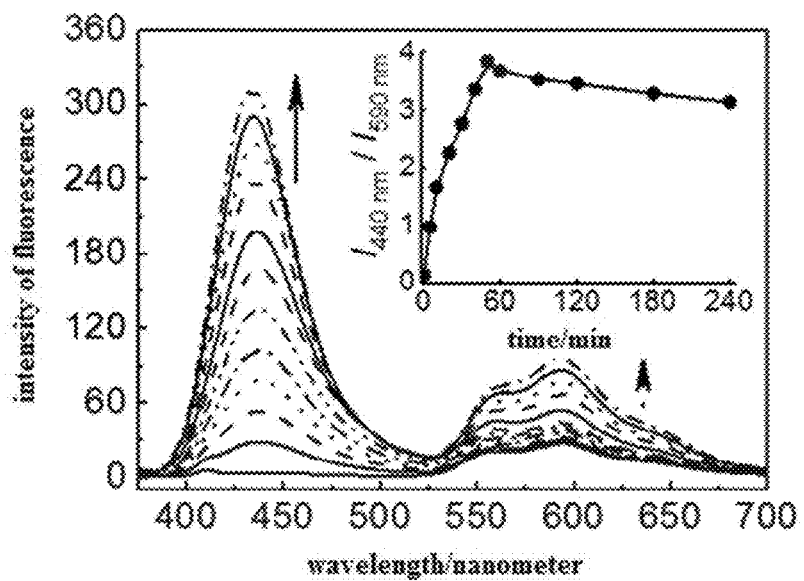
FIG. 14 shows the fluorescence change curve during the reaction of preparing the antibody-drug conjugate in Example 8.

In the reaction progress, the conjugation efficiency of the block copolymer was monitored by fluorescence emission intensity, and the results were shown in FIG. 13 and FIG. 14, wherein FIG. 13 showed the fluorescence change curve during the reaction of preparing antibody-probe conjugate, and FIG. 14 showed the fluorescence change curve during the reaction of preparing antibody-drug conjugate.

Figure 15:
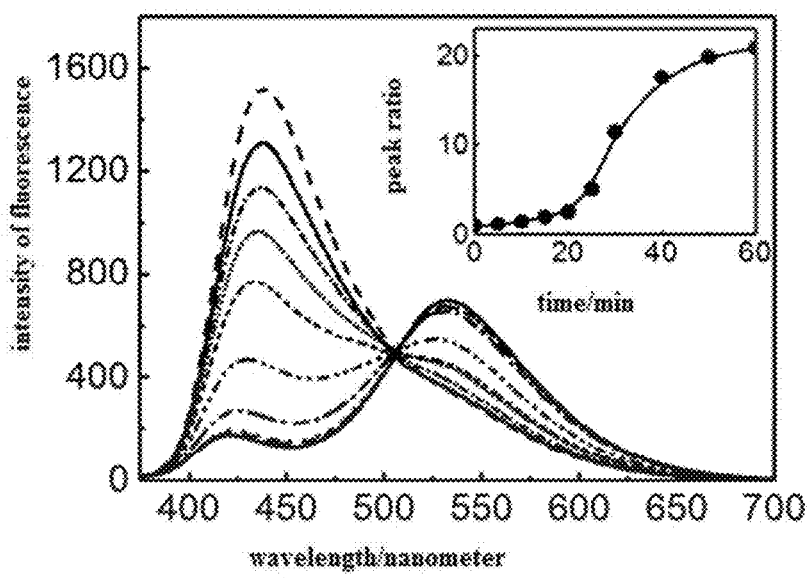
FIG. 15 shows the fluorescence change in the enzyme detection process of the antibody-probe conjugate prepared in Example 8.

FIG. 15 showed the fluorescence change in the enzyme detection process of the—antibody-probe conjugate prepared in Example 8; QNAM-C1-ACEA antibody-probe conjugate was prepared from NADPH/NQO1 in water system, and it can be seen that the emission intensity of NAM (at ~530 nm) significantly increased, accompanying with a large scale decrease of the emission intensity of C1 at ~435 nm. In a culture time of about 1 h, a change of about 20 times the FRET ratio (intensity ratio of two emission peaks) can be seen (see inset). The above results indicated the occurrence of an efficient FRET process between the C1 coumarin linkage bond and the enzymatic-produced NAM residue. The sharp change (about 20 times) of the FRET ratio after QNAM-C1-ACEA conjugate reacted with NQO1 indicated that the antibody-probe conjugate can be used to detect the concentration of NQO1 enzyme.

Figure 16:
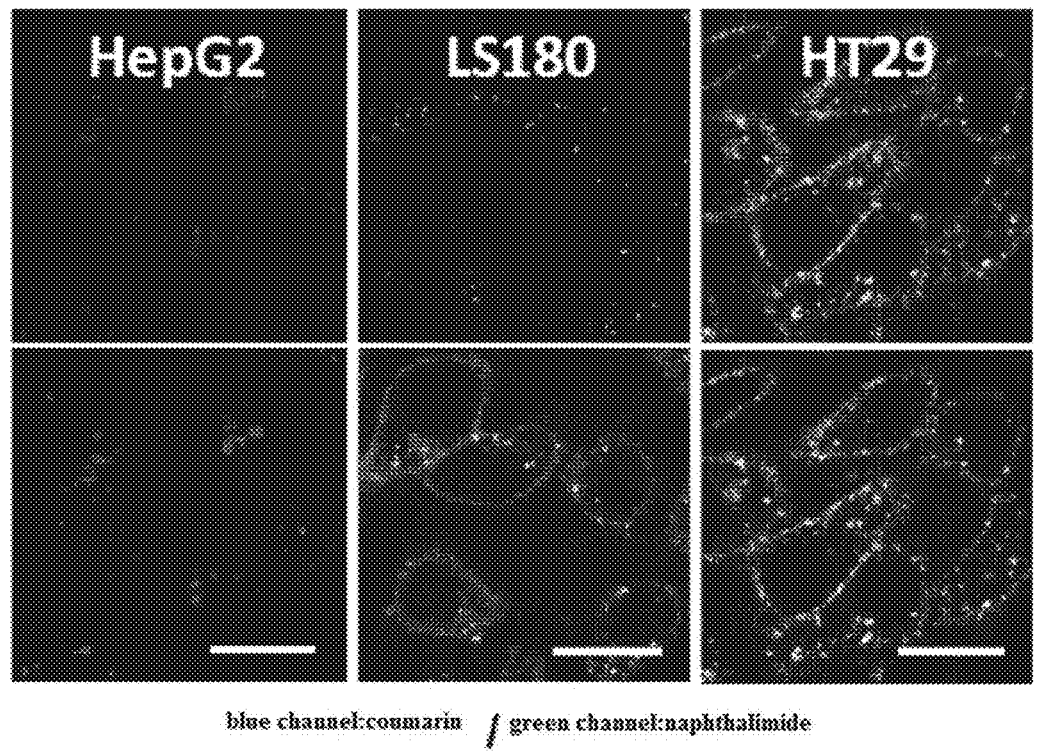
FIG. 16 shows the detection of intracellular carcinoembryonic antigen and quinone oxidoreductase of the antibody-probe conjugate prepared in Example 8

FIG. 16 showed the detection of intracellular carcinoembryonic antigen and quinone oxidoreductase of the antibody-probe conjugate prepared in Example 8. Viable HepG2 cells (lacking CEA and NQO1), LS180 cells (normal CEA and lacking NQO1) and HT29 cells (normal CEA and normal NQO1) were co-cultured with QNAM-C1-ACEA antibody-probe conjugate. After the co-culture, the confocal laser scanning microscope (CLSM) image of LS180 cells with normal CEA and lacking NOQ1 showed that there were intermittent blue luminous points of C1 coumarin and few NAM green emission signals in the cells. These results indicated that QNAM-C1-ACEA was obviously up-taken by cells and had an intracellular stability due to the lack of NQO1 in cytoplasm. For colon cancer cells (ht29) with CEA and NQO1, the green channel NAM emission was obviously enhanced, and was almost co-located with the blue channel emission of C1 coumarin linkage. The intensity of the later was significantly decreased due to the occurance of FRET process. However, HepG2 cells lacking CEA and NQO1 treated with QNAM-C1-ACEA showed very low blue and green emission. Since NQO1 enzyme was mainly located in the cytoplasm of certain types of cancer cells, the above results showed that the QNAM-C1-ACEA conjugate-probe could only display strong green channel emission in form of "AND" logic gate (i.e., in the presence of CEA and NQO1 at the same time).

Figure 17:
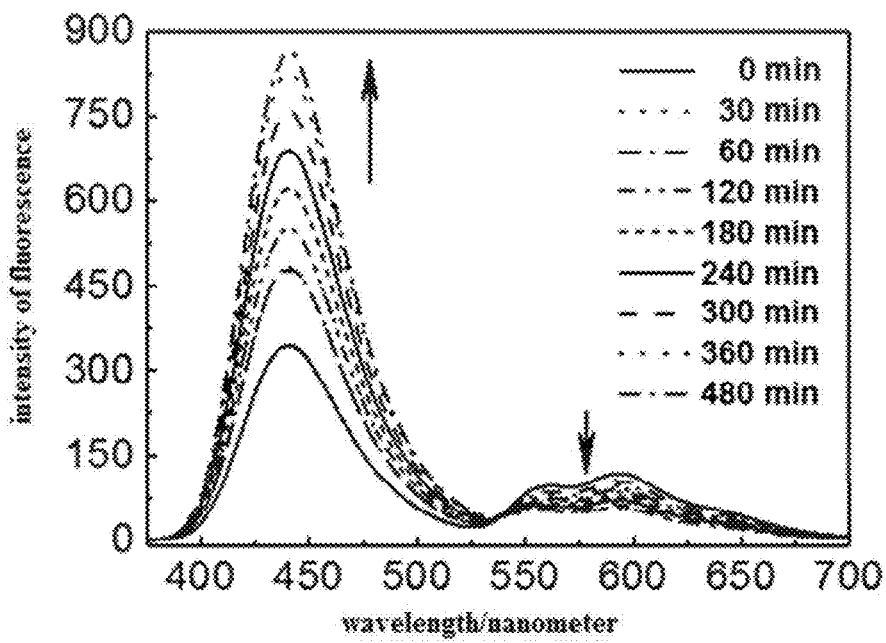
FIG. 17 shows the fluorescence change in the drug release process triggered by nitroreductase of the antibody-drug conjugate prepared in Example 8.

FIG. 17 showed the fluorescence change in the drug release process triggered by nitroreductase of the antibody-drug conjugate prepared in Example 8. When DOX-C1-ACEA was co-cultured with nitroreductase/reduced coenzyme II, the conjugated doxorubicin drug continuously linearly released along with time. The release of doxorubicin accompanied with significant increase in the emission of C1 linkage bond at 435 nm, and obvious decrease in the emission of doxorubicin at 590 nm. These clearly indicated the breakage of drug-antibody conjugate and the destruction of FRET process.

Example 9 Intracellular Cell Imaging

HT29 or HepG2 cell (~10⁵) culture solution was spread on a 35 mm glass-bottom petri dish overnight, and then DOX-C1-ACEA and the cells were co-cultured at 37° C. for 24 h. The cells were washed with PBS (3×1 mL) and DMEM culture solution, and the cell fluorescence imaging should be carried out under Leica SP5 confocal microscopy. The C1 group contained in the sample was stimulated at 405 nm, acridine orange was stimulated at 488 nm, and DOX was stimulated at 543 nm.

Figure 18:
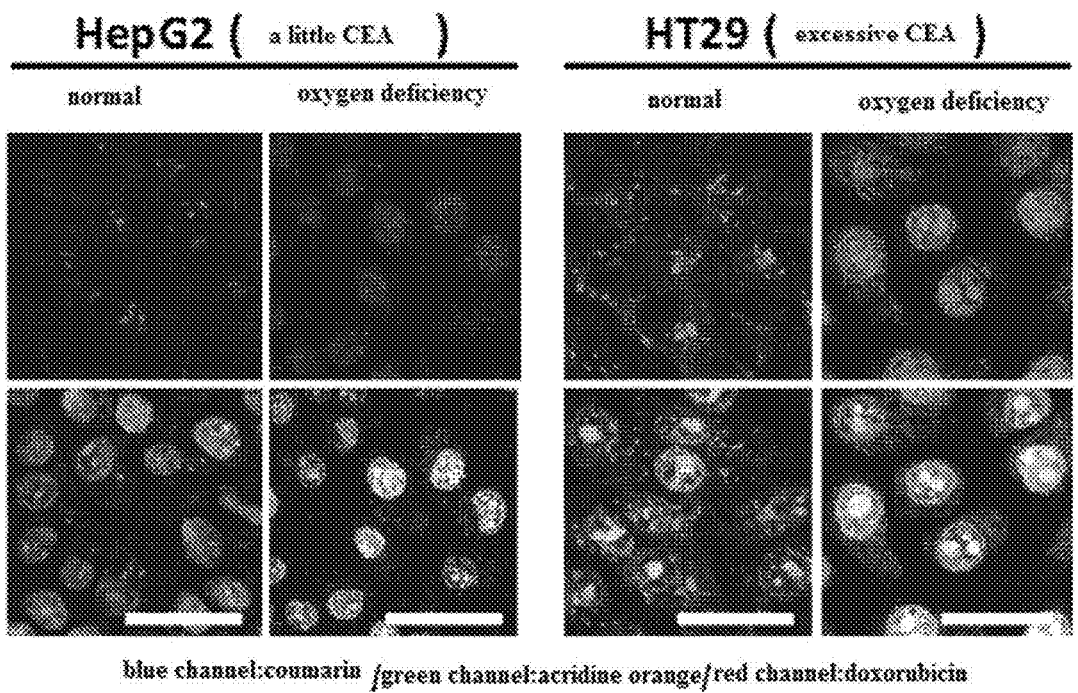
FIG. 18 shows drug release process triggered by intracellular nitroreductase containing carcino-embryonic antigen of the antibody-drug conjugate prepared in Example 9.

FIG. 18 showed drug release process triggered by intracellular nitroreductase containing carcino-embryonic antigen of the antibody-drug conjugate prepared in Example 9. When the HT29 cells containing CEA were cultured with DOX-C1-ACEA conjugate under normal oxygen content, intermittent strong green emission of C1 and red dot emission of doxorubicin were observed in the cytoplasm by a confocal microscopy, and blue/green emissions could be co-located with each other. In contrast, as for the HepG2 cells lacking CEA, the blue fluorescence intensity of the C1 coumarin linkage bonds was only 22% in the HT29. If HT29 was co-cultured with DOX-C1-ACEA for 4 h under anoxic conditions, the obvious doxorubicin red emission could be well co-located with acridine orange dyed cell nucleus. In addition, blue emission of the uncontinuous C1-ACEA residue was only co-located in the cytoplasm. The above results indicated that the CEA antigen on the surface of some cancer cells (such as HT29) facilitated the cellular uptake of DOX-C1-ACEA conjugate, and it is easy to trigger the release of doxorubicin in the cells under hypoxic conditions, which was related to the microenvironment of tumor tissue.

It can be concluded from the above examples that the drug-antibody conjugate and the probe-antibody conjugate were constructed by connecting molecule C1, and the conjugation efficiency was in-situ monitored by fluorescence.

Example 10 Fluorescence Conjugate of BSA and PEG$_{227}$-N$_3$ Mediated by Bifunctional Fluorescent Molecule C1

Bovine serum albumin BSA (498 mg, 7.5 μmol) was dissolved in phosphate buffer solution (PBS) (70 mL, pH 6.5, 0.1M, containing 1 mM EDTA). At the same time, tri-(2-chloroethyl)phosphate hydrochloride (TCEP.HCl) (21.5 mg, 75 μmol) was dissolved in PBS (2.5 mL), and the resultant was added dropwise in the above BSA solution. 4 h later, the solution was dialyzed with deionized water for 24 h (2.0 kDa molecular weight cut-off), and freeze dried to give the BSA$_{red}$.

The BSA or BSA$_{red}$ (4 mg, 0.06 μmol) was dissolved in PBS (0.9 mL, pH 7.0, 50 mM). C1 (0.6 μmol, dissolving in 0.1 mL DMSO), PEG$_{227}$-N$_3$ (6 mg, 0.6 μmol) and CuSO$_4$/Na-ascorbate (1/5 molar ratio) were added in the solution, stirred at 25° C. for different times, and the conjugation progress was tested by in-situ monitoring the change of fluorescence emission intensity at about ~420 nm. After reaching the set time, 80 μL of the sample solution was taken out, and diluted with 2 mL PBS. Copper ionic adsorption resin (American Ocean Chemical Company, 100 mg) was quickly added to remove the copper ions. After vibrating for 5 min, the suspension was filtered out through a 0.22 μm sterile syringe injector before further SDS-PAGE test.

Figure 19:
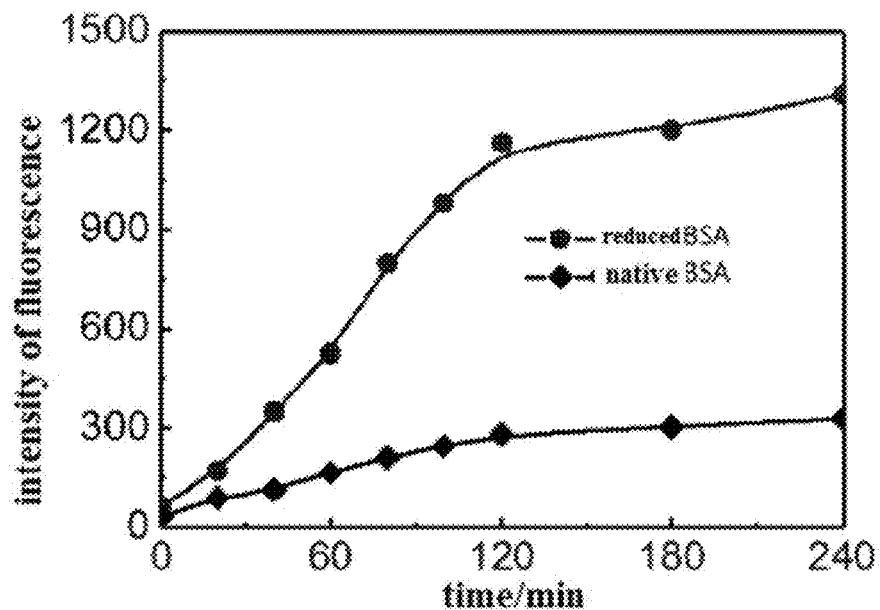
FIG. 19 shows the fluorescence change during the conjugation process of the bovine serum albumin-polyethylene glycol conjugate prepared in Example 10.
Figure 20:
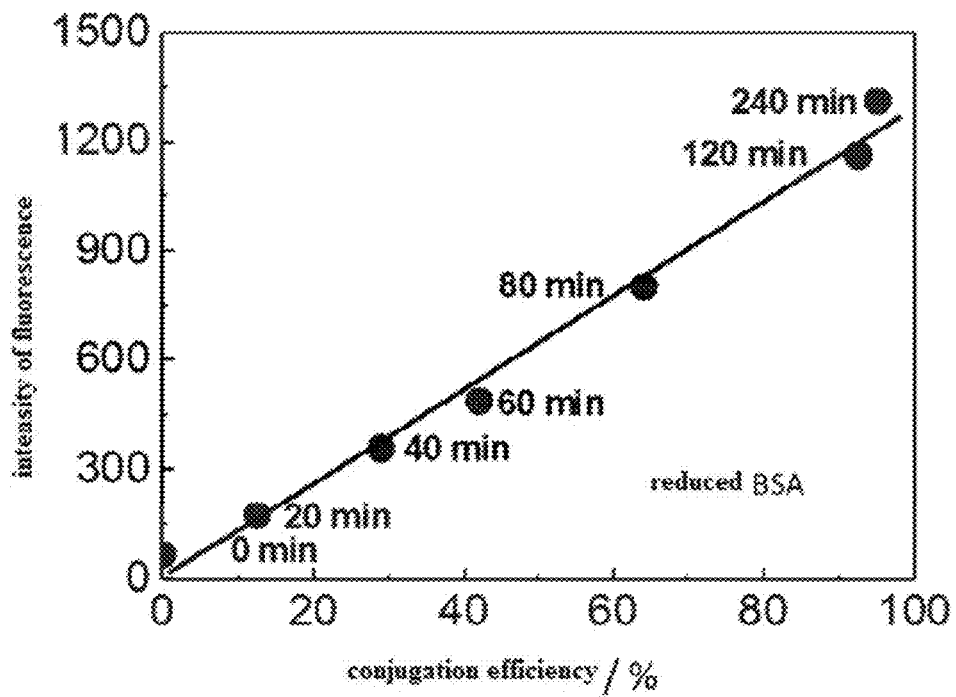
FIG. 20 shows the relationship between the fluorescence change and conjugation efficiency of the bovine serum albumin-polyethylene glycol conjugate prepared in Example 10.

In the reaction process, the fluorescence change was shown in FIG. 19, and the relationship between fluorescence change and the conjugation efficiency was shown in FIG. 20.

Gel electrophoresis experiment: SDS-PAGE experiment was carried out with a gel electrophoresis apparatus (Bio-Rad). BSA-PEG conjugate-containing solution (80 μL) and 20 μL SDS-PAGE loading buffer were mixed, and 15.0 wt % polyacrylamide gel was used according to the standard scheme. The gel electrophoresis band can be directly observed under ultraviolet light (365 nm) or the white light irradiation of UVP EC3 imaging system (dyed with coomassie brilliant blue).

Figure 21:
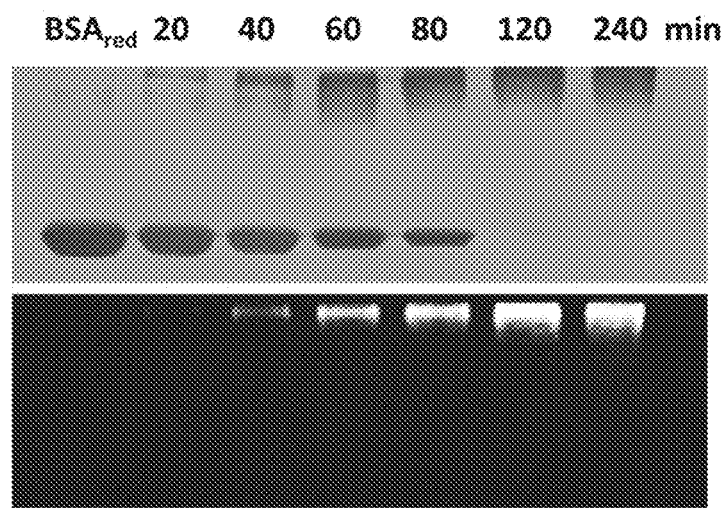
FIG. 21 shows the sodium dodecyl sulfate-polyacrylamide gel electrophoretogram of the bovine serum albumin-polyethylene glycol conjugate prepared in Example 10.

FIG. 21 showed the gel electrophoretogram.

Example 11 Fluorescence Conjugate of Salcatonin (sCT) and PEG$_{227}$-N$_3$ Mediated by Bifunctional Fluorescence Molecule C1

TCEP.HCl (14.2 mg, 50 μmol) was dissolved in PBS (2 mL, pH 7.0, 50 mM). 40 μL the above solution (containing 1 μmol TCEP.HCl) was added in a bottle containing salcatonin (sCT, 1.7 mg, 0.5 μmol PBS (9 mL, pH 7.0, 0.05 M)), and stirred at room temperature. The RP-HPLC analysis showed that the Cys$^1$-Cys$^7$ disulfide bond was quantitatively reduced within about 30 min.

200 μL C1 in DMSO (containing 0.2 μmol C1), PEG$_{227}$-N$_3$ (10.0 mg, 1.0 μmol) and CuSO$_4$/Na-ascorbate (1/5 molar ratio) were added in reduced sCT (0.1 μmol, dissolving in 1.8 mL PBS buffer solution), and stirred at 25° C. for different times. The conjugation process was tested by in-situ monitoring the fluorescence emission intensity at ~420 nm. 4 h later, copper ionic adsorption resin (American Ocean Chemical Company, 100 mg) was quickly added to remove the copper ions. After vibrating for 5 min, the suspension was filtered out through a 0.22 μm sterile syringe injector. 80 μL solution was used to carry out the SDS-PAGE experiment, and the rest solution was dialyzed for 24 h before the RP-HPLC experiment.

Figure 22:
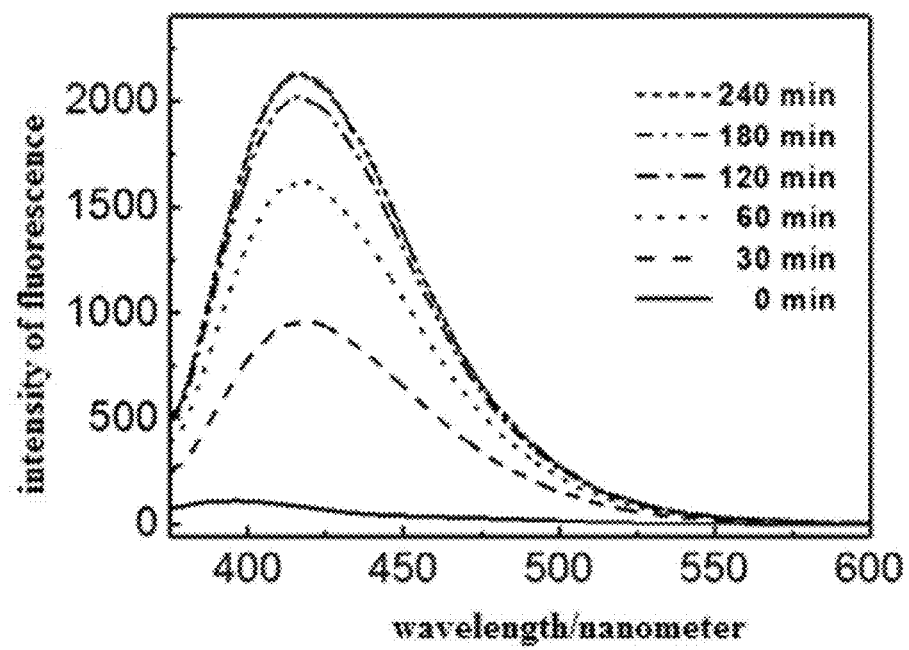
FIG. 22 shows the fluorescence change during the conjugation process of the salcatonin-polyethylene glycol conjugate in Example 11

In the reaction process, the fluorescence change was shown in FIG. 22.

Figure 23:
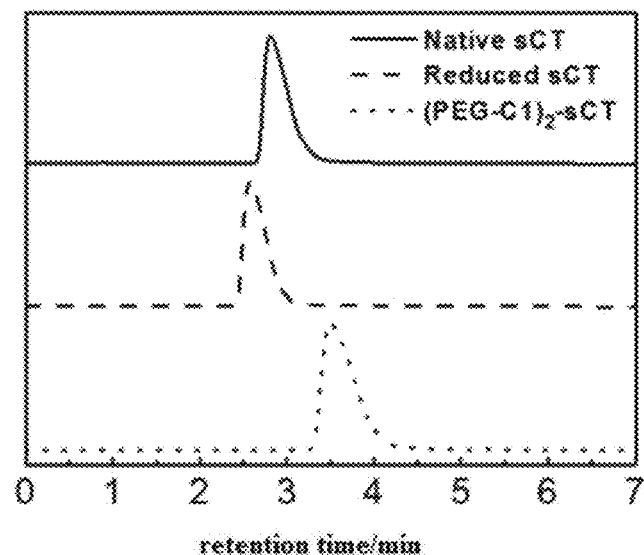
FIG. 23 shows the size exclusion chromatography of the salcatonin-polyethylene glycol conjugate prepared in Example 11.

The molecular weight of the prepared protein-polymer conjugate was tested by size exclusion chromatography, and the size exclusion chromatography was shown in FIG. 23.

Gel electrophoresis experiment: SDS-PAGE experiment was carried out with a gel electrophoresis apparatus (Bio-Rad). SCT-PEG conjugate-containing solution (80 μL) and 20 μL SDS-PAGE loading buffer were mixed. 15.0 wt % polyacrylamide gel was used according to the standard scheme. The gel electrophoresis band can be directly observed under ultraviolet light (365 nm) or the white light irradiation of UVP EC3 imaging system (dyed with coomassie brilliant blue).

Figure 24:
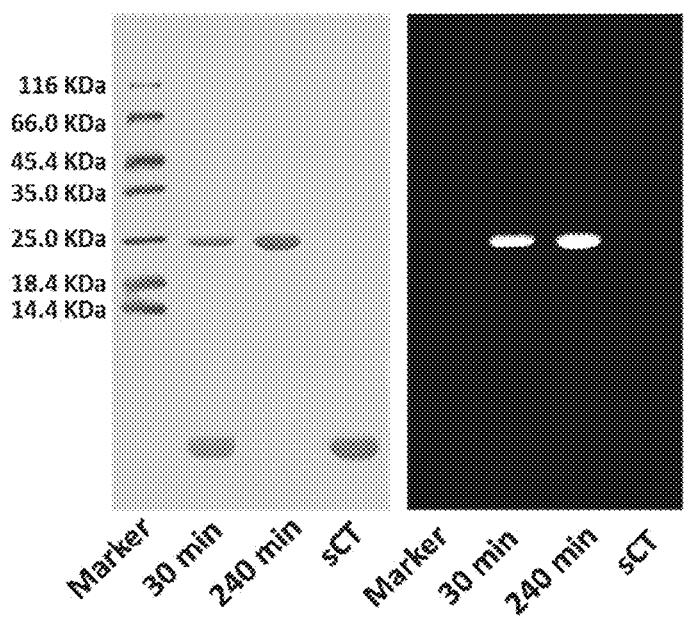
FIG. 24 shows the sodium dodecyl sulfate-polyacrylamide gel electrophoretogram of the salcatonin-polyethylene glycol conjugate prepared in Example 11.

The gel electrophoretogram was shown in FIG. 24.

Example 12 Synthesis OF Azide-Functionalized PTMC (PTMC-N$_3$)

Recrystallized trimethylene carbonate (TMC) monomer (500 mg, 4.9 mmol) was dissolved in dry CH$_2$Cl$_2$ (1 mL). Then 3-azido-1-propanol (24 mg, 0.24 mmol) and 1,3-dicyclohexylurea (DCU, 8 mg, 0.05 mmol) were added dropwise in dry CH$_2$Cl$_2$ (1 mL). The reaction mixture was stirred in nitrogen atmosphere at room temperature for 12 h. Acetic acid was used to quench the reaction. The reaction mixture was diluted with tetrahydrofuran, and precipitated for three times with excess cold methanol. The precipitation was dried in a vacuum drying oven, to give a white powder PTMC-N$_3$ (160 mg, yield 30.5%). The actual degree of polymerization of PTMC was calculated by 1H NMR to be 14, and thus abbreviated as PTMC14-N$_3$.

Example 13 Fluorescence Conjugate of PVGLIG Polypeptide and PTMC$_{14}$-N$_3$ Mediated by Bifunctional Fluorescent Molecule C1

PTMC$_{14}$-N$_3$ (7.5 mg, 5.0 μmol) and C1 (1.5 mg, 5.1 μmol) were dissolved in DMSO (1.8 mL). PVGLIG (8.1 mg, 10.1 μmol) and CuSO$_4$/ascorbic acid (1/5 molar ratio) were dissolved in 0.2 mL deionized water, which was then added in the above mixture. The reaction system was stirred at 25° C. The conjugation process was tested in-situ by fluorescence. After co-culturing for about 3 h, copper ionic adsorption resin (American Ocean Chemical Company, 200 mg) was quickly added to remove the copper ions. After vibrating for 5 min, the suspension was filtered out with a 0.22 μm sterile syringe injector. The filtrate was precipitated with excess cold acetonitrile. The precipitation was collected by centrifugation, followed by drying overnight in a vacuum drying oven.

Example 14 Preparation of PVGLIG-C1-PTMC$_{14}$ Polymer Vesicle

PVGLIG-C1-PTMC$_{14}$ (2 mg) was dissolved in 1 mL DMSO. The resultant was added in a 15 mL bottle containing magnetic stirring bar, stirred at room temperature for 3 h. Under the condition of stirring (about 500 rpm), 9 mL deionized water was added within about 20 s. Stirring was continued for 5 h and then the resultant was dialyzed (molecular weight cut-off 3.5 kDa) for 24 h with deionized water.

Figure 25:
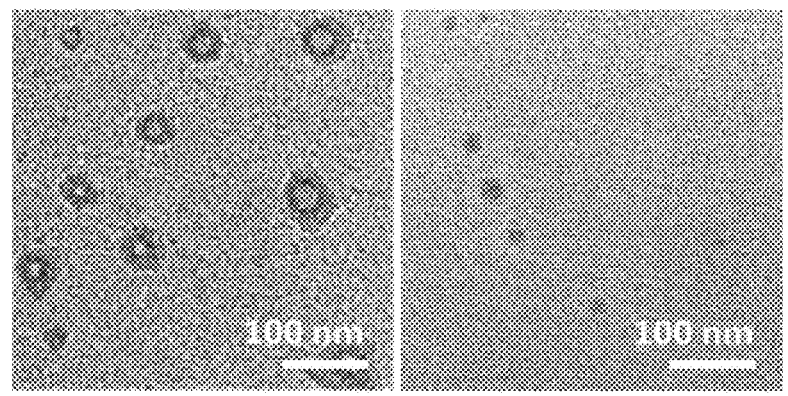
FIG. 25 shows a transmission electron microscope image of the vesicles in water prepared in Example 14.

The transmission electron microscope image of the prepared vesicle in water was shown in FIG. 25.

Example 15 PVGLIG-C1-PTMC$_{14}$ Polymer Vesicle Embedded Doxorubicin Hydrochloride PVGLIG-C1-PTMC$_{14}$ (2 mg) was dissolved in 1 mL DMSO, added in a 15 mL bottle containing magnetic stirring bar. Under conditions of stirring, DOX.HCl-containing deionized water (5 g/L, 2 mL) was firstly added in, and the remaining 7 mL deionized water was added at the same speed. Stirring was continued for 5 h, and then the resultant was dialyzed (molecular weight cut-off was 3.5 kDa) with deionized water for 24 h. The loading content of DOX was about 8.0 wt %.

Figure 26:
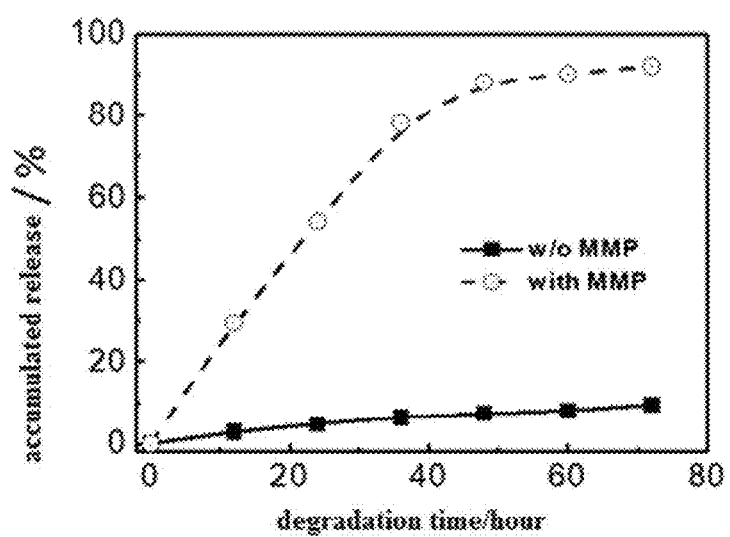
FIG. 26 shows the drug controlled release curve in Example 15.

The drug controlled release curve was shown in FIG. 26.

It can be concluded from the above examples that the conjugation efficiency of the above protein/polypeptide-polymer conjugate prepared in the present disclosure could be in-situ monitored by fluorescence emission intensity, and the protein/polypeptide-polymer could be used for the delivery of therapeutic polypeptide and anti-cancer drug.

The above descriptions of the embodiments are merely to assist in understanding the method and the core idea of the present disclosure. It should be noted that those skilled in the art can make various modifications and improvements to the present disclosure without departing from the principle of the present disclosure, and these modifications and improvements also fall within the protection scope of the claims of the present disclosure.

The invention claimed is:

1. An antibody-drug/probe conjugate having fluorescence emission properties, wherein it has a structure as shown in Formula I-2:

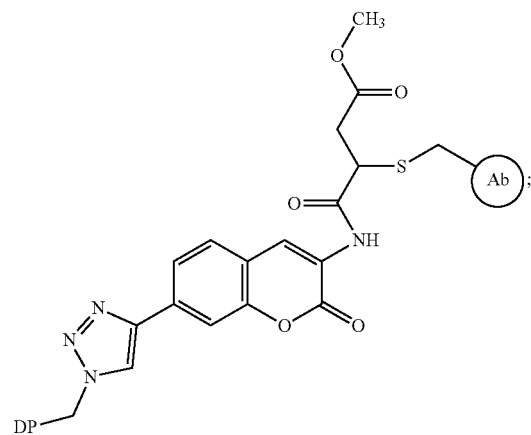

Formula I-2 wherein,
Ab is an antibody, and DP is a fluorescence probe or a drug molecule.

2. The antibody-drug/probe conjugate having fluorescence emission properties according to claim 1, wherein it has a structure as shown in Formula II-2:

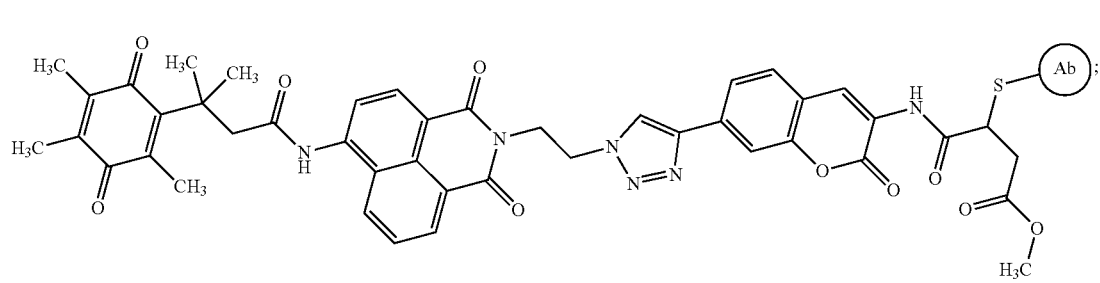

Formula II-2 wherein Ab is a carcinoembryonic antigen monoclonal antibody or Herceptin.

3. The antibody-drug/probe conjugate having fluorescence emission properties according to claim 2, wherein it is prepared by a method comprising steps of:
performing a Michael reaction and a click reaction on a monoclonal antibody, a fluorescence probe A containing an azide group and a bifunctional fluorescent molecule D, to obtain the antibody-probe conjugate as shown in Formula II-2;

Formula II-2 wherein, the monoclonal antibody is a carcinoembryonic antigen monoclonal antibody or Herceptin containing a sulfhydryl group.

4. The antibody-drug/probe conjugate having fluorescence emission properties according to claim 3, wherein a conjugation efficiency of the antibody-drug/probe conjugate is in-situ monitored by fluorescence emission intensity.

5. The antibody-drug/probe conjugate having fluorescence emission properties according to claim 2, which is used as a reaction indicator of an antigen and a quinone oxidoreductase.

6. The antibody-drug/probe conjugate having fluorescence emission properties according to claim 1, wherein it has a structure as shown in Formula III:

Formula III wherein, DOX is doxorubicin, and Ab is a carcinoembryonic antigen monoclonal antibody or Herceptin.

7. The antibody-drug/probe conjugate having fluorescence emission properties according to claim 6, wherein it is prepared by a method comprising steps of:
performing a Michael reaction and a click reaction on a monoclonal antibody, a prodrug molecule E containing an azide group and a bifunctional fluorescent molecule D, to obtain the antibody-drug conjugate as shown in Formula III;

-continued

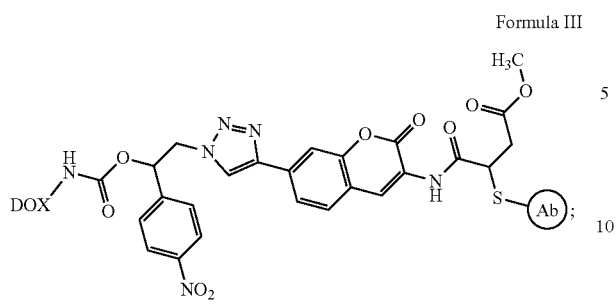
Formula III wherein DOX is doxorubicin, and the monoclonal antibody is a carcinoembryonic antigen monoclonal antibody or Herceptin containing a sulfhydryl group.

8. The antibody-drug/probe conjugate having fluorescence emission properties according to claim 7, wherein a conjugation efficiency of the antibody-drug/probe conjugate is in-situ monitored by fluorescence emission intensity.

9. The antibody-drug/probe conjugate having fluorescence emission properties according to claim 6, which is used as a fluorescent indicator in real-time monitoring drug release.

10. The antibody-drug/probe conjugate having fluorescence emission properties according to claim 6, which is used as a targeted drug release carrier.

11. A protein/polypeptide-polymer conjugate having fluorescence emission properties, wherein it has a structure as shown in Formula I-3:

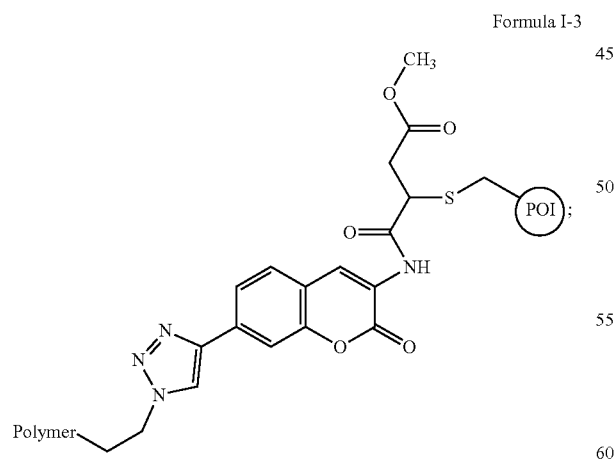
Formula I-3 wherein, POI is a protein or a polypeptide; and Polymer is a polymer.

12. The protein/polypeptide-polymer conjugate having fluorescence emission properties according to claim 11, wherein it has a structure as shown in Formula I-a:

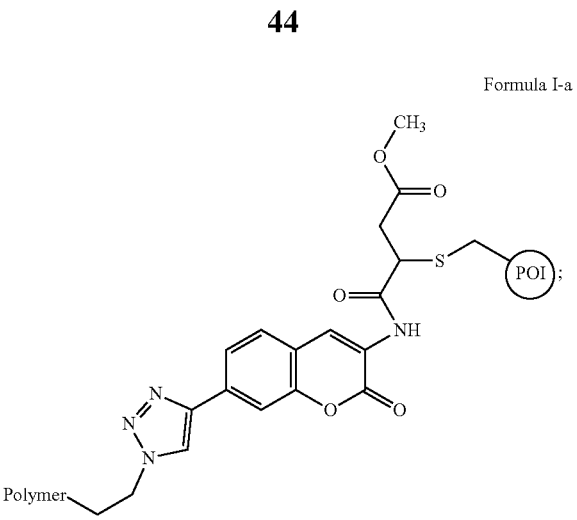
Formula I-a wherein, POI is a bovine serum albumin or a salcatonin, and Polymer is a polyethylene glycol.

13. The protein/polypeptide-polymer conjugate having fluorescence emission properties according to claim 12, wherein it is prepared by a method comprising-steps of:
performing a Michael reaction and a click reaction on a bovine serum albumin containing a sulfhydryl group, a polyethylene glycol containing an azide end group and compound D, to obtain a protein-polymer conjugate as shown in Formula I-a;

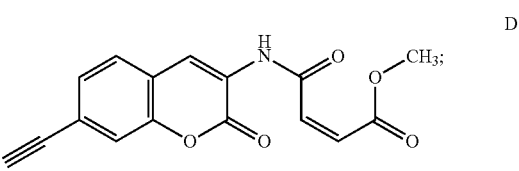 [SMILES: C#Cc1ccc2cc(NC(=O)/C=C\C(=O)OC)c(=O)oc2c1]
D

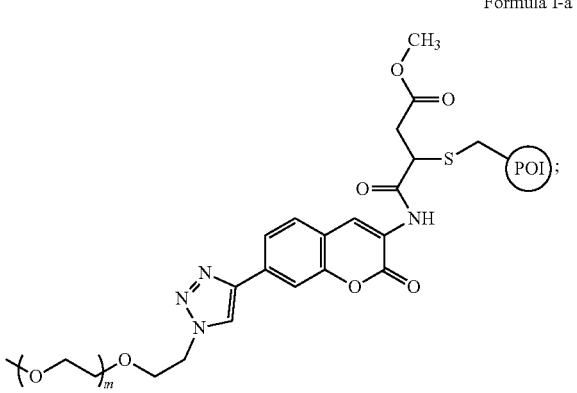
Formula I-a wherein POI is a bovine serum albumin, and m is 23-445;
or it comprises steps of:
performing a Michael reaction and a click reaction on a salcatonin containing a sulfhydryl group, a polyethylene glycol containing an azide end group and compound D, to obtain a protein-polymer conjugate as shown in Formula I-a;
wherein POI is a salcatonin; and m is 23-445.

14. The protein/polypeptide-polymer conjugate having fluorescence emission properties according to claim 11, wherein it has a structure as shown in Formula I-b:

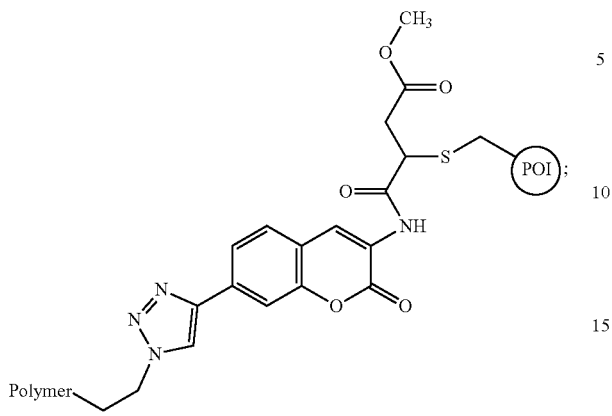

wherein, POI is a matrix metalloproteinase cleavable polypeptide, and Polymer is a polytrimethylene carbonate.

15. The protein/polypeptide-polymer conjugate having fluorescence emission properties according to claim 14, wherein it is prepared by a method comprising steps of:
performing a Michael reaction and a click reaction on a matrix metalloproteinase cleavable polypeptide as shown in Formula J, a polytrimethylene carbonate containing an azide end group as shown in Formula K and compound D, to obtain the polypeptide-polymer conjugate as shown in Formula I-b;

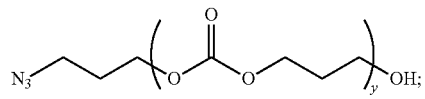

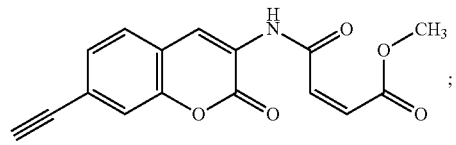

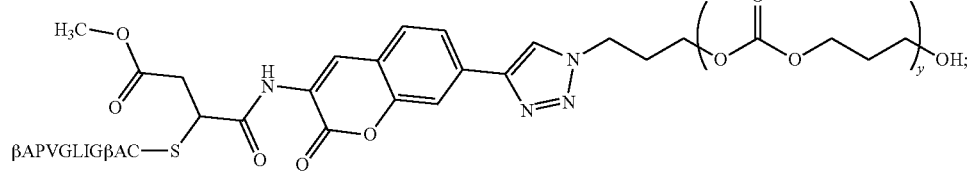

wherein y is 10-55.

16. The protein/polypeptide-polymer conjugate having fluorescence emission properties according to claim 13, wherein a conjugation efficiency of the conjugate is in-situ monitored by fluorescence emission intensity.

17. The protein/polypeptide-polymer conjugate having fluorescence emission properties according to claim 15, wherein a conjugation efficiency of the conjugate is in-situ monitored by fluorescence emission intensity.

* * * * *